US005532131A

United States Patent [19]

Lewis

[11] Patent Number: 5,532,131
[45] Date of Patent: Jul. 2, 1996

[54] FORENSICALLY-ACCEPTABLE DETERMINATIONS OF GESTATIONAL FETAL EXPOSURE TO DRUGS AND OTHER CHEMICAL AGENTS

[75] Inventor: Douglas E. Lewis, 1131 W. Oakdale, Chicago, Ill. 60657

[73] Assignee: Douglas Edward Lewis, Chicago, Ill.

[21] Appl. No.: 242,185

[22] Filed: May 13, 1994

Related U.S. Application Data

[63] Continuation-in-part of Ser. No. 115,902, Sep. 1, 1993, Pat. No. 5,326,708, which is a continuation of Ser. No. 843,526, Feb. 28, 1992, abandoned.

[51] Int. Cl.$^6$ ............................ G01N 33/53; G01N 33/00
[52] U.S. Cl. ............................ 435/7.9; 436/92; 436/161
[58] Field of Search ............................ 435/7.9, 803, 962, 435/973; 436/92, 161, 172, 173, 804, 816, 901

[56] References Cited

U.S. PATENT DOCUMENTS

| | | | |
|---|---|---|---|
| 5,015,589 | 5/1991 | Ostrea, Jr. | 436/92 |
| 5,185,267 | 2/1993 | Ostrea, Jr. | 436/92 |

OTHER PUBLICATIONS

Murphey et al., Quantitation of benzoylnorcgonine and other cocaine metabolites in meconium by high-performance liquid chromatography, J. Chromatog. 613:330–335, 1993.

Clark et al., "Analysis of Cocaine and Benzoylecgonine in Meconium of Infants Born to Cocaine Dependent Mothers," Clinical Chemistry, Jul., 1990, vol. 36, No. 6, Abstract 0327, p. 1022.

Rosenzweig et al., "Neonatal Drugs of Abuse Screening in Meconium, A Comparison Between Abbott TDx and Syva ETZ," Clinical Chemistry, Jul., 1990, vol. 36, No. 6, Abstract 0334, p. 1023.

Jennison, "An Evaluation of Clean Screen Extraction Columns for the Analysis of Benzoylecgonine," Clinical Chemistry, Jul., 1990, vol. 36, No. 6, Abstract 0335, p. 1023.

Clark et al., "The Analysis of Cocaine and Benzoylecgonine in Meconium," Journal of Analytical Toxicology, Jul./Aug. 1992, vol. 16, pp. 261–263.

*Primary Examiner*—Mary E. Mosher
*Assistant Examiner*—Donna C. Wortman
*Attorney, Agent, or Firm*—Hill, Steadman & Simpson

[57] ABSTRACT

New and improved methods for collecting neonatal meconium samples, preparing meconium specimens for testing and for chemically analyzing neonatal meconium samples to determine their chemical composition are provided. A novel extraction method is employed in accordance with the invention to provide a non-aqueous, concentrated "cocktail" meconium extract containing substantially all of many possible target analytes in a single extraction step. Preliminary screening by fluorescence polarization immunoassay methods may be performed on the cocktail extract to qualitatively determine the presence of the target analytes in the meconium sample. If a positive preliminary result is obtained, new and improved quantitative GC/MS confirmatory procedures are provided by this invention to unequivocally identify and quantitate the amount of target analyte present in the sample in terms of nanograms of analyte per gram of meconium tested.

16 Claims, No Drawings

FORENSICALLY-ACCEPTABLE DETERMINATIONS OF GESTATIONAL FETAL EXPOSURE TO DRUGS AND OTHER CHEMICAL AGENTS

This application is a continuation-in-part of application Ser. No. 08/115,902, filed Sep. 1, 1993, now U.S. Pat. No. 5,326,708, issued Jul. 3, 1994, which is a continuation of application Ser. No. 07/843,526, filed Feb. 28, 1992, abandoned.

BACKGROUND OF THE INVENTION

The present invention generally relates to drug testing methods for determining maternal drug use during pregnancy and fetal exposure to drugs in utero. More particularly, it relates to new and improved qualitative and quantitative methods for testing neonatal meconium tissue samples to provide unequivocal evidence of prenatal exposure to chemical agents such as drugs of abuse by identifying and quantifying the presence of these chemical agents or their known metabolites in the newborn meconium tissue samples.

There is growing concern in society today about the increasing numbers of newborn infants who are born in an undesirably unhealthy condition because they have been exposed to harmful chemical agents in utero. Perhaps the most widespread concern surrounds an apparent increase in maternal abuse of addictive drugs, both licit and illicit, during pregnancy. Primary interest has been focused on the so-called drugs of abuse, e.g., cocaine, opiates, including heroin, morphine and codeine, amphetamines, phencyclidine (PCP), and marijuana-related compounds, such as tetrahydrocannabinoids (THCs). Secondarily, other so-called legally available substances such as barbiturates, muscle relaxers, anti-anxiety agents, i.e. diazepam or lorazepam, alcohol, nicotine and other chemical agents may be shown to affect the health of a developing fetus. Although the present invention is primarily directed to drugs and their known metabolites, other chemical agents capable of becoming protein-bound may also be of interest. For example, gestational exposure to certain insecticides, herbicides, industrial chemicals, air pollutants and water pollutants may also be shown to adversely affect the exposed fetus in utero and the health of the newborn infant.

Maternal abuse, use or exposure to several known chemical agents, such as addictive drugs has been reported to lead to decreased birthsize and birthweight, decreased head circumference, decreased gestational duration and in a few cases, congenital defects. Generally, infants born to drug addicted and/or using mothers may be characterized by being compromised, in ill-health, exhibiting an early failure to thrive and possibly may be expected to show significant developmental delays or anomalies if they survive after the first few days and weeks. For example, neuronal damage may not become recognizable until later in the life of the child.

Proper medical care and treatment for the special needs of these disadvantaged individuals frequently requires that treating physicians and nurses be advised of the fact that the neonate has been exposed in utero. Moreover, the identity of which drug or chemical agent the child has been exposed to as a fetus may also be critical to early courses of treatment and ultimate survival. If latent neuronal damage was caused leading to real or apparent learning disabilities, early detection and possession of the information can really help that newborn in many ways. If learning disability problems are inevitable or likely, early extra educational efforts to assist the child may help to reduce or eliminate any adverse effects to that child. Moreover, if the child is identified early as disabled or handicapped due to in utero drug exposure, Federal educational and social assistance may be available to the child to help with the costs of raising, educating and caring for the child. The financial and human costs of delivering the high-risk neonatal medical care and continuing medical and social care and services for these infants in increasingly higher numbers is staggering.

Recent studies show that maternal abuse of addictive drugs during pregnancy is widespread and increasing. The National Association for Perinatal Addiction Research and Education estimated that approximately 11% of women studied in 36 hospitals had used illicit drugs during pregnancy. In regional areas where drug abuse is known to be a significant problem, the estimates are considerably higher. Recently, in one southern California hospital, authorities estimated that they had delivered at least about 20,000 drug addicted babies in one year. Similarly, a Chicago Municipal hospital estimated delivery of over 12,000 drug-exposed or addicted newborns per year. Conservative estimates by public health experts indicate that there are at least about 500,000 drug-exposed neonates born each year in the United States, about 10% of the annual birth rate.

The severity of this public health and societal problem has come to the attention of several legislatures. Some jurisdictions proscribe the use of addictive drugs during pregnancy and define the presence of such drugs in the neonate as a prima facie child abuse, thereby creating an immediate state interest in the care and custody of these infants. In addition to increased demands for intensive medical care and management, health care providers must also act responsibly in accordance with newly defined and increased duties imposed on them by these new statutes and regulations. Health care providers in some jurisdictions have a duty to screen and identify the drug exposed neonates and their mothers.

Earlier efforts to identify and assess those mothers who used or abused drugs during pregnancy and who thereby exposed their infant newborns to drugs in utero have included obtaining oral admissions from the mother, blood testing and urine testing. Oral histories, as has been mentioned above, are generally not forthcoming or reliable. Testing of blood tissue samples for the presence of drugs or their metabolites is generally time consuming and expensive. The recent AIDS epidemic has made collection, testing and handling of blood tissue samples unwise and undesirable. In addition, the target analytes of the drugs of abuse, typically looked for will not be present in either maternal bloodstream or the neonate's bloodstream even only six hours after the mother has taken the drug. Usually the first neonatal blood samples aren't taken until about 12–24 hours after delivery. Accordingly, blood testing of an infant newborn is expected to provide a ridiculously large number of false negative results.

Urine testing is also problematic for several reasons. Collecting adequate sample specimens from premature infants is difficult at best. Unless the fetus was exposed to the drug within one to three days immediately prior to delivery which is generally unlikely, urine screens frequently yield false negative results. Accordingly, urinalysis is generally inconclusive at best.

More recently, it has been demonstrated that meconium tissue formed in the intestines of a fetus in utero may provide the best physical evidence of maternal drug use. Meconium is a complicated heterogeneous tissue including a matrix of proteinaceous and cellular solids capable of binding, adsorbing and storing various chemical agents per se and/or their respective metabolic end products. Meconium is continuously formed and stored in the fetal intestines from late in the first trimester of gestation i.e., from between about 12–16 weeks, until birth.

Meconium forms the first several excreta of a newborn infant until a change to transitional milk stools is observed. Meconium tissue may therefore act as a biological time-capsule, in that each infant's meconium may reveal the history of the fetus in utero in terms of its exposure to various chemicals which become bound in the meconium matrix as the meconium is formed. The contents of neonatal meconium may provide evidence of exposure to drugs or other chemical agents back in time during the pregnancy, possibly as early as the later part of the first trimester and definitely from the second and third trimesters immediately before birth. The importance of the meconium tissue is that this precious sample is a one-shot deal. Unless the meconium is properly collected and analyzed a great deal of once-in-a-lifetime information is permanently lost. The personal and social implications of not having the important information the tissue can provide are very serious.

A major problem associated with collecting and studying meconium tissue is that it is extremely difficult to work with. Meconium has a thick visco-elastic nature that does not readily lend itself to typical sample analysis methods and equipment.

In U.S. Pat. No. 5,015,589 to Ostrea Jr., two distinct methods for testing a meconium sample to qualitatively determine whether or not it contains morphine and/or cocaine metabolites or cannabinoids, respectively, are described. In the assay procedure to qualitatively screen infant meconium for the presence of morphine or cocaine metabolites, a 0.5 to 1.0 gram sample of infant meconium is diluted more than 2 to 1 with an aqueous hydrochloric acid solution. The acidified and diluted sample is vortexed and poured through a glass wool filter to remove gross particulates. The filtrate is centrifuged and an aliquot portion is analyzed for morphine metabolites and cocaine metabolites by radioimmunoassay.

In the Ostrea Jr. method for qualitatively determining the presence of marijuana metabolites, a neonatal meconium sample is admixed with absolute methanol, vortexed and permitted to stand at room temperature for several minutes. Thereafter, the mixture is filtered, centrifuged and an aliquot portion of the supernate is tested for cannabinoid metabolites by radioimmunoassay.

The Ostrea Jr. methods described in U.S. Pat. No. 5,015,589 suffer from a number of shortcomings. The determinations are qualitative at best and do not offer unequivocal quantitative evidence of prenatal drug exposure needed to meet current forensic standards. Moreover, the qualitative procedures described are generally not reproducible in practice. This is believed to be primarily caused by the broad compositional variations in the heterogeneous meconium tissue in general. For example, a positive or negative result may depend on the location from which the aliquot portion of the meconium sample was taken in relation to the overall meconium specimen. This distributional variation within a single sample can often lead to false negative test results. Furthermore, the procedures are not particularly sensitive in practice. In accordance with the Ostrea Jr. method, a small sample of meconium is diluted with an aqueous acid. Ostrea Jr.'s acid reagents dilute trace amounts of target analytes found in the sample to a large degree. After the immunoassay reagents are added, the target unknowns are diluted even further, often below the minimum detectable concentrations of the immunoassay reagents themselves. The aqueous mineral acids employed are so strongly acid that they not only hydrolyze and denature the meconium matrix to release target analytes into aqueous solution, these acids may also de-nature the recognizable structure of the metabolites being assayed, further lowering their effective detectable concentrations.

Poor sensitivity and non-reproducibility experienced with the Ostrea Jr. method may also result from the fact that Ostrea Jr. requires a glass wool filtration step to remove gross particulates from the acidified mixture. It has independently been observed that untreated glass surfaces, such as those presented by the glass wool filters employed in the Ostrea Jr. method, are reactive with the sample analytes and absorb and bind target substances, thereby taking them out of the assay solutions. Untreated glass surfaces can absorb as much as 10 nanograms of drug or other metabolite for every square centimeter of untreated glass surface area that the drug containing solution is exposed to.

Another disadvantage to Ostrea Jr.'s methods is that different extraction procedures and steps must be performed on the same meconium tissue for each target analyte in order to only make what is an essentially unreliable qualitative determination for that analyte. In a commercial setting, too many separate procedures and duplicative steps disadvantageously increase the time and costs needed to implement the Ostrea Jr. method. Finally, the Ostrea Jr. patent describes making their screening determinations using radio immunoassays which are undesirable because costly special care, handling and disposal steps are required in order to use these radioactive materials.

Another prior art method for screening neonatal meconium samples is described by Rosenzweig et al. in an abstract appearing in *Clinical Chemistry*, Vol. 36, No. 6, (1990) at page 1023, Abstract No. 0334. In the method described in this abstract, evidence of drugs and drug metabolites may be qualitatively determined for amphetamine, cocaine metabolite, morphine metabolite and cannabinoid metabolite in neonatal meconium samples by non-radioactive immunoassay methods. In accordance with this screening method, a meconium sample is extracted with methanol, centrifuged and the supernatant is filtered through filter paper. The volume of the filtrate is reduced by evaporation and reconstituted in a phosphate buffer. The buffered sample is then analyzed by enzymatic colorimetric immunoassay or by a fluorescence polarization immunoassay method.

The non-radioactive screening methods described by Rosenzweig also have disadvantages in terms of reliability and sensitivity. The meconium methanol extract is generally too highly colored for direct reading in a colorimetric read assay. Ten fold dilutions are needed to achieve workable readability which reduces analyte concentration to at or below sensitivity limits to the assays. The method includes a paper-filter filtration step which has also been shown to act as a drug sponge undesirably absorbing target analyte out of the sample. Also, the Rosenzweig methods described in the abstract are only qualitative screens and do not provide the unequivocal quantitative evidence needed. Furthermore no special sample preparation steps are described or suggested so that the disclosed method also suffers from lot to lot variability for samples taken from the same patient sample.

In another abstract published in *Clinical Chemistry*, Vol. 36, No. 6 (1990) at page 1022, Abstract No. 0327, Clark et al, describe a first quantitative procedure for determining quantities of cocaine and its major metabolite, benzoylecgonine, from meconium samples. The Clark et al. method includes extracting cocaine and its metabolites from a sample of meconium with methanol and centrifuging to remove solids. The supernatant is concentrated by evaporation, reconstituted with phosphate buffer and extracted with a solid phase cation exchange column. Solid phase bound analytes are eluted into an organic solvent, derivatized and injected into a GC/MS instrument in selective ion monitoring mode. Unknown patient samples were compared with spiked negative samples and quantitative results were obtained from the standard curve. The GC/MS method was reported by Clark et al. to be able to detect cocaine or its metabolite at levels as low as 300 ng of drug per gram of meconium tested.

The earlier GC/MS confirmatory method described by Clark et al. made some progress toward providing a quantitative meconium testing method but suffers from several drawbacks. In practice, a methanol extract as described by Clark et al. results in a meconium sample fluid containing neutral fats and free fatty acids which frequently clog the solid phase extraction columns. The Clark et al. procedures also do not address variability of the meconium samples per se and do not provide for variable dispersability of the meconium in the methanol so that non-reproducible results are often obtained. The sensitivity for these confirmatory procedures was stated to be a drug concentration of about 300 ng/g of meconium for cocaine and benzoylecgonine. Nevertheless, the ability to detect even smaller amounts of drugs or their metabolites and determining exposure as early as within the second and first trimesters of pregnancy is still desired. The Clark et al. article specifically describes a quantitative GC/MS method for cocaine only with limited sensitivity. No teachings or suggestions are provided for making quantitative GC/MS assays for meconium samples for other drugs of abuse, their respective metabolites or other chemical agents of interest.

U.S. Pat. No. 5,185,267 (Ostrea) discloses another procedure for detecting maternally transferred drug metabolites in a newborn infant which is provided by weighing out a 0.2 gram portion of infant meconium and adding 5 mls of an aqueous phosphate buffer and methanol solution (<30% methanol) to the sample. This is a substantial dilution of the sample with water. The sample is agitated, then centrifuged. The supernatant fluid is transferred to a microcentrifuge vessel and centrifuged again. A portion of the supernatant is assayed for drug analytes by enzyme immunoassay methods.

Accordingly, to overcome the limitations of the prior art procedures and methods, it is an object of the present invention to provide new and improved testing methods for obtaining unequivocal evidence of prenatal exposure to selected target analytes, such as the drugs of abuse and their metabolites, as well as other chemical agents.

It is another object of the present invention to provide faster, less expensive and more reliable methods for testing neonatal meconium samples to qualitatively and quantitatively determine gestational fetal exposure to not only cocaine and its metabolites, but also to opiates, amphetamines, phencyclidines and cannabinoids, as well as other licit and illicit drug analytes.

It is still another object of the present invention to provide new and improved methods for collecting and preparing neonatal meconium tissue samples for further testing to provide improved analyte separation and recovery.

It is still another object of the present invention to provide a new and improved method for making a smooth, substantially uniform time-averaged meconium tissue product for further testing to reduce the incidence of false negative results and aliquot to aliquot variability for neonatal meconium tissue specimens.

It is another object of the present invention to provide a new and improved method for liberating and extracting substantially all target analyte values of interest from a neonatal meconium sample, in relatively concentrated form in a single step, for use in a number of analytical testing procedures.

It is a further object of the present invention to provide new and improved methods meeting currently accepted forensic standards to unequivocally identify and quantitate the presence of drugs of abuse in meconium adapted for use on a commercial scale in a commercial testing laboratory.

It is still another object of the present invention to improve the quality of medical care for newborn infants in our society by providing fast, inexpensive and reliable methods for early detection of those newborns exposed to various harmful chemical agents while a fetus in utero.

SUMMARY OF THE INVENTION

In accordance with these and other objects, the present invention broadly comprises new and improved methods for collecting meconium samples, preparing meconium specimens appropriate for testing, and chemically analyzing neonatal meconium samples to determine their chemical composition. In accordance with the first aspect of the invention, new and improved methods are provided for collecting the meconium tissue of a subject neonate in a manner which effectively preserves the chemical information stored in the meconium tissue and to promote maximum recovery of sample target analyte.

More particularly, in accordance with this aspect of the invention, a plurality of meconium excreta or bowel movements are collected from a subject newborn infant in diapers specially lined with a removable liner material selected for its non-absorbent and non-adherent properties with respect to the meconium tissue. Each incremental meconium sample is transferred from the lined diaper to a storage container and kept under refrigeration until the last meconium excreta movement has been made by the infant. Meconium has a very characteristic bluish-gray-green color and a rubbery elastic texture which differs greatly from the first transitional milk stool made after the infant begins postpartum feeding. The first transitional milk stool is characterized by being loosely formed and bright yellow tan in color. Accordingly, collecting meconium until the first transitional milk stool is observed is an easy end point to identify. The production of meconium excreta by infants varies from infant to infant but can occur from birth up to as many as 10 days after birth. Collecting all of the meconium samples from a single baby and storing them in a single refrigerated container provides an extended "time window" tissue sample which may be analyzed to provide evidence of drug exposure.

In accordance with the preferred embodiment, the collection and preparation procedure further includes the step of smoothing out the meconium samples to allow target analytes such as drugs which are not uniformly distributed through the meconium to be more thoroughly and evenly distributed in a prepared sample. Redistributing drug analytes to form a time-averaged tissue sample is achieved by rendering the meconium into a smooth substantially uniform non-striated paste-like mass. Pre-processing pooled meconium specimens enhances reproducibility of testing results for the tissue and avoids the occurrence of false negatives brought about by distributional anomalies inherent in the nature of meconium tissue itself.

In accordance with another aspect, the present invention provides a new and improved method for preparing a concentrated neonatal meconium extract. The concentrated meconium extract is thereafter employed as the sample fluid for performing qualitative screen testing to determine whether one or more target analytes are present in the original meconium sample. Thereafter, in accordance with the overall method of the present invention, if a positive result from the preliminary screen testing is obtained, a quantitative test procedure is undertaken to definitively identify and quantify target analytes present in the meconium sample in quantitative terms, i.e., terms of nanograms of analyte per gram of meconium.

More particularly, the new and improved method for preparing a concentrated neonatal meconium extract comprises providing a sample of newborn meconium suspected of containing at least one target analyte. A minor effective amount of a substantially non-aqueous volatile organic acid is added to the prepared test sample to form a first mixture. The first mixture is agitated for a time sufficient to release substantially all of the at least one target analyte from the meconium sample substantially without diluting the sample with water.

In accordance with an especially preferred method, after the volatile organic acid is added to a pre-processed meconium specimen sample, the pooled and collected meconium tissue is next finely subdivided and disrupted by high shear mixing, preferably by means of a shearing bladed instrument, such as a tissue homogenizer, to disrupt the cellular and other protein structures of the meconium matrix. Shearing of the acidified pre-processed sample renders it more amenable to subsequent processing steps. Tissue homogenizing improves liberation of the target analytes and more thoroughly distributes the unbound target analytes evenly and uniformly within the overall tissue specimen to avoid sample to sample variations in subsequent testing. Preferably, after homogenizing, the meconium test sample is a substantially uniform meconium tissue sample homogenate having a finely divided, average particle size of less than about 10 microns, and especially preferably between about 2.0 to about 5.0 microns to facilitate release and extraction of the target analytes.

The volatile organic acid agent for use herein is generally acidic enough to begin to denature the meconium matrix to release the target analytes in liberated or unbound form. The agitation of the first mixture should be fairly vigorous and result in a substantially uniform first liquid homogenate. After the first liquid homogenate is obtained, a minor effective amount of a volatile organic solvent is added to the first homogenate to form a two-phase mixture including an organic phase and a second phase. The two-phase mixture is agitated and thoroughly mixed for a time sufficient to permit substantially all of the released target analyte to be extracted and collected into the organic phase. Thereafter the organic phase is separated from the second phase to provide the concentrated extract. The volatile organic extract may readily be concentrated further by evaporating the volatile organic components in a sample concentrator.

In accordance with an important aspect of this method the concentrated meconium extract comprises a "cocktail" extract which contains substantially all of the various target analytes being looked for. For example, if drug abuse testing is the object of the procedure, the volatile organic acid/ volatile organic solvent treatment step results in a concentrated non-aqueous extract containing substantially all of the target drug and drug metabolite analytes in a single extraction step. For example, target analytes of cocaine or its benzoylecgonine metabolite, opiates including morphine and codeine, amphetamines, marijuana metabolites and phencyclidine all comprise protein-bound target analytes which are successfully collectively extracted into the "cocktail" extract in accordance with the new and improved method with advantageously good recovery.

An important feature of this aspect of the invention is that the target analyte values extracted from the meconium matrix are not unnecessarily diluted with water but are extracted in relatively concentrated form. The target unknowns may be readily concentrated even further upon standing or by evaporating in a sample evaporator in a short period of time of less than three hours. The volatile extract provides an important advantage when scaling up drug testing in a commercial setting for a commercial laboratory because prolonged aqueous dilution and prolonged or high-temperature drying steps are avoided.

In accordance with another especially preferred aspect of the present invention a method is provided for preparing a concentrated neonatal meconium extract containing both basic and acidic-neutral target analytes present, if any, and a sample of infant meconium suspected of containing such analytes. This preferred embodiment includes addition of substantially non-aqueous methanol solution to a test sample of meconium and subsequent agitation of the mixture to form a substantially uniform homogenate and to denature the protein matrix and release the drug bound to protein into the methanol phase. The methanol phase is separated from the homogenate such as by centrifugation and the methanol phase containing the target analytes is subjected to further extraction procedures. These further extraction procedures include the use of mixed mode extraction columns such as cationic and $C_8$ reversed phase resins and anionic and $C_8$ reversed phase resins. This particular method is particularly useful to screen a wide range of both basic and acidic-neutral analytes by a variety of methods. For instance, cocaine metabolites, opiates cannibinoids, amphetamines, phencyclidine, methadone, barbituates, and propoxyphene to name but a few analytes can, to the extent present, be tested by enzyme multiplied immunoassay, fluorescence polarization immunoassay and gas chromatography/mass spectrometry.

After the concentrated "cocktail" extract is obtained, in accordance with the method of this invention, aliquot portions of the extract are preliminarily screened or tested in an homogeneous immunoassay method to qualitatively determine whether or not the extract contains the target analytes of interest. In accordance with the preferred embodiment of the invention, the target analytes will be the drugs of abuse and their respective metabolites selected from cocaine, amphetamines, opiates, phencyclidine and cannabinoids and/or their respective metabolites. The preferred immunoassay technique is by fluorescence polarization immunoassay (FPIA). If a positive result is obtained from the preliminary assay screen, then another aliquot portion of the prepared meconium tissue sample is subjected to a further independent quantitative confirmation procedure which includes an extraction procedure specific for that analyte. The confirmatory aliquot of sample is spiked with labelled analyte analogs which are extracted selectively with their respective target analytes. The extracted analytes and analogs are derivatized and subjected to quantitative analysis using gas chromatographic mass spectrometric (GC/MS) equipment.

In accordance with this confirmatory aspect, the present invention provides new and improved confirmatory (GC/MS) quantitative assay procedures for not only cocaine and its metabolite but other drugs of abuse such as the opiates, amphetamines, cannabinoids and phencyclidine as well. The earlier "cocktail" extract prepared in the preliminary qualitative screening represents an effective compromise at getting all of the target analytes out of an aliquot portion of the sample in a single extraction step to provide an easy one-step approach. However, the preliminary extraction reagents and methods may not necessarily provide the highest rate of extraction for each given target analyte in the drugs of abuse group. Accordingly, for the confirmatory procedures, a second aliquot portion of the prepared meconium tissue sample is taken and a second extraction procedure is run which is designed to be specific for the target analyte to now be quantitatively determined.

More particularly, the particular extraction procedure for the GC/MS confirmatory extraction step is chosen to maximize the extraction recovery of that particular target analyte already tested positively to be present in the qualitative preliminary screen. The exact confirmatory extraction procedures for each target analyte will be described in greater detail hereinafter. Generally, the opiates and amphetamines are extracted using a liquid/liquid extraction. The improved cocaine quantitative analysis procedure and the cannabinoid and phencyclidine confirmatory procedures each employ solid phase extraction columns to provide an appropriate extract fluid for GC/MS quantitative analysis.

The new and improved confirmatory extraction procedures and GC/MS quantitative analysis methods of the present invention now provide unequivocal evidence of prenatal drug exposure in a forensically acceptable manner to confirm the presence of cocaine metabolites, THC metabolites, opiates, amphetamines and PCP in the neonate which were heretofore unavailable for meconium testing. The methods of the invention may also be used to quantify and provide unequivocal forensic evidence of exposure to other chemical agents. The methods of the invention provide cheaper, faster and more sensitive assays which may be readily adapted to a commercial laboratory setting. The new and improved preliminary cocktail screening extract procedure results in a ten-fold improvement in sensitivity over prior art aqueous acid extraction and methanol extraction methods.

Other objects and advantages of the present invention will become apparent from the following Detailed Description and illustrative working Examples.

DETAILED DESCRIPTION OF THE INVENTION

In greater detail now, the first aspects of the new and improved methods of this invention relate to the proper collection and preparation of the neonatal meconium tissue samples preparatory to further testing. As has been mentioned above, the advantage of testing meconium for drugs of abuse or other target analytes lies in the fact that meconium is gradually formed and thereafter is stored in the intestines of the infant until gradually expelled in the immediate postpartum time period. Overall, the entire meconium content of the infant newborn provides stored chemical information developed over most of the gestational period of development for the infant. Accurate and sensitive chemical analysis for small amounts of specific target analytes present in the meconium samples requires the striated, non-uniform collected meconium specimens to first be vigorously mashed and stirred, to re-distribute the contents of the pooled meconium matrix so that a substantially smooth, evenly distributed putty-like pre-processed meconium product is formed. During collection, pooling and processing, care should be taken to preserve the maximum amounts of target analytes and not to lose sample analyte to various surfaces the samples may come in contact with at these stages of preparation.

In accordance with the preferred embodiment, a complete meconium sample is collected from a subject newborn infant suspected of gestational exposure to one or more target substances by collecting and pooling each meconium stool produced by that infant from birth until the first appearance of transitional or milk stool appears. The meconium tissue is collected in the babies' diapers and because the meconium tissue and any contained target analyte may become absorbed on or into the diaper surfaces, in accordance with a preferred embodiment herein, each of the babies' diapers is lined with a liner sheet of water-proof, non-absorbent material. The liner sheet may generally comprise any sheet material having surface properties which effectively resist or avoid adsorption, absorption or reaction with the meconium sample. Plastic materials are preferred for forming the diaper liners and polyethylene sheets are especially preferred. Generally, in addition to not absorbing sample, the diaper liner sheet should be able to maintain its structural integrity in the wet diaper environment.

Each meconium bowel movement for the subject infant is collected on the diaper liner and thereafter stored in a lidded storage container having a volume capable of receiving all meconium samples produced by the subject neonate, typically from about 2.5 to about 5.0 grams. Meconium generally has an apparent density such that about one teaspoon of meconium approximately weighs about one gram. A minimum of at least about 2.0 grams of meconium overall should be collected from each neonate.

The collected meconium specimens should be transferred from the diaper liner to a non-surface reactive lidded storage jar or vessel and kept under refrigerated conditions until sample collection for that infant is complete. In accordance with the preferred embodiment, the storage vessel is selected to be made from polypropylene. The storage container generally should not be made of untreated glass or other sample-reactive material to prevent sample and target analyte from becoming absorbed or adsorbed by the surfaces of the glass container. Collected and pooled specimens stored in the container may be stored under refrigeration at temperatures of about 2° to about 8° C. for up to 30 days without any significant analyte loss. For longer storage times, pooled specimens should be stored frozen at −15° C. or lower.

After all of the subject infant's meconium has been collected, then in accordance with the preferred embodiments, the pooled meconium tissue at room temperature is pre-processed to provide a time-averaged tissue sample to correct for the non-homogeneous nature of drug distribution in the meconium mass. Vigorous stirring and mixing of the sample is performed to improve the distribution of the target analyte in the meconium matrix. In practice, it has been found that the meconium matrix is tenaciously rubbery, striated and non-uniform and mixing should be thorough enough to be effective to achieve a substantially smooth, evenly distributed non-striated sample, characterized by low sample to sample variation.

In accordance with the method of the present invention, the smooth pre-processed meconium product is thereafter subjected to a two-step analytical approach and procedure to unequivocally identify and quantify the presence of one or more target analytes in the meconium of the subject infant. A first preliminary qualitative immunoassay screening procedure is performed to identify the presence of target analyte(s) in the patient sample. For those infants testing positive for target analyte(s) in the preliminary screening, a second quantitative determination by a GC/MS procedure is run to quantify the amount of each specific target analyte present in the sample. The results of the GC/MS confirmatory procedures report the drug or other target analyte findings in acceptable quantitative units such as nanograms of target analyte per gram of meconium tested.

In accordance with a special feature of the new and improved method of the present invention, the preferred pre-processed meconium tissue product is subjected to a new and improved extraction procedure to liberate substantially all of the target analytes from the meconium matrix and form a concentrated non-aqueous meconium "cocktail" extract.

More particularly, in accordance with the preliminary screening procedure, an aliquot portion of the pre-processed meconium sample is subjected to a generalized extraction treatment procedure to liberate and separate the target analytes from the meconium matrix in concentrated form for further testing. The extraction procedure should be fast, accurate and efficient and well suited to commercial laboratory settings where large numbers of samples must be tested at high through-put rates. The extraction should liberate substantially all target analytes of interest in a single efficient step.

In accordance with the preferred embodiment of the present invention, a new and improved group extraction step is performed by placing about a 1 gram sample of the pre-processed meconium product into a polypropylene tube (16 by 125). A minor effective amount of a substantially non-aqueous, volatile organic acid reagent is added to the pre-processed sample in the tube to form a first mixture. The volatile organic acid is selected to be effective to precipitate proteins and neutralize lipids and fatty acids to aid in separation of the analyte values from the meconium matrix.

The meconium sample in accordance with the preferred embodiment, should be subjected to high shear, bladed processing, to break up the meconium matrix into cellular and sub-cellular sized fragments in the acid treatment step to insure substantially complete liberation of all target analyte(s). The high shear processing treatment preferably results in a smooth, substantially uniform finely-divided soft paste-like product having an average particle size of less than about 10 microns. Especially preferably the pre-processed meconium tissue product will be processed until a substantially smooth, non-striated homogeneous meconium product having an average particle size of between about 2.0 to about 5.0 microns is obtained.

In accordance with this preferred aspect of the invention, pre-processing of the pooled meconium samples to finely-divided, evenly distributed homogeneous form may be accomplished using a commercially available tissue homogenizer. A tissue homogenizer is an apparatus including a hollow cylindrical shaft having a small diameter so that it may be fully inserted into a narrow tube such as a test tube or sample collection vial. A rotatable blade mounted on a concentric axial shaft within the cylindrical outer tube, shears the tissue against the blades, itself and the interior surface of the tissue homogenizer tube to form the disrupted, finely-divided processed meconium product. The tissue homogenizer is moved through the meconium sample until processing and homogenization are substantially complete, typically in a matter of about 5 minutes or less. A preferred commercially available tissue homogenizer for use herein is an OMNI 5000 model tissue homogenizer available from OMNI International, Inc. In practice, it has been discovered that acid addition followed by mixing, even vortex mixing, is not as effective at obtaining liberation of target analytes from the meconium matrix. Failure to homogenize or process in a fractionating, disruptive partitioning manner, has been observed to result in substantially lower recoveries of target analytes.

It has also now been discovered that often significant quantities of analyte remain in the fat or lipid segments of the meconium. In the past lipids have not advantageously been extracted because of the extract reagents used or because of the handling methods employed. In accordance with this invention, the volatile organic acid should extract the lipids and neutral fats in the first instance together with the target analytes to liberate substantially all target analyte values from the meconium matrix. The acid should exhibit good volatility, i.e. high evaporation rates at or above room temperatures. The acid liberating agent should not react with the analyte per se. Moreover, the volatile organic acid should not liberate harmful or toxic fumes on evaporation or volatilization.

In testing a number of non-aqueous organic acid candidates, the best acids were found to be propionic and glacial acetic acids. Propionic acid was slower to evaporate and accordingly the especially preferred non-aqueous volatile organic acid for use in the method of the present invention is glacial acetic acid. The preferred glacial acetic acid component should be added in a minor effective amount of about 2 to 5 ml. of concentrated glacial acetic acid per gram of sample and preferably about 3 mls. of acetic acid are added.

Thereafter, in accordance with the preferred method of this invention, a minor effective amount of a volatile organic solvent is added to the first liquid homogenate to form a two-phase mixture which includes an organic phase and a second phase. The volatile organic solvent should be effective to dissolve and collect the liberated analyte values in the meconium sample and preferably will solubilize or dissolve fats or lipids to insure that all of the target analyte is carried over into the organic phase. The two-phase mixture thus formed is thoroughly mixed for a time sufficient to permit all of the released target analyte values to be extracted and collected into the organic phase. The volatile organic solvent selected should be fast and cheap and volatilize readily to provide a concentrated analyte extract. The organic solvent should also selectively extract all the target analyte and some of the free fats to promote maximum recovery of the target analyte from the meconium matrix. The organic solvent should be polar enough to extract metabolites of morphine or cannabinoids such as theglucuronide forms. In accordance with the present invention, the preferred volatile organic solvent in terms of volatility and cost and extractive properties is acetone, although acetonitrile or certain dialkylethers may also be used.

In accordance with this intermediate step, the two-phase mixture is thoroughly mixed by vortexing and thereafter is mixed on a sample mixer for a period from about 3 to 10 minutes, preferably for about 5 minutes. Generally, the two-phase mixture should be agitated sufficiently to permit all of the target analyte(s) to be extracted and collected into the organic phase.

In accordance with an especially preferred embodiment, the volatile organic solvent reagent will also include a minor effective amount of a glass anti-binding agent in the form of a secondary or tertiary amine having a molecular weight of from about 100 to about 400 which is non-reactive with the target analyte or other sample components. The preferred glass anti-binding agent for use herein comprises diphenylamine. In addition, all glassware to which the sample or extraction reagents come in contact should be silanized before sample materials are placed therein. A more complete description of silanizing treatment is set forth hereinafter.

After the two-phase mixture is thoroughly mixed by vortexing or otherwise for a period of about 5 minutes, the organic phase is separated from the second phase by any suitable separation method. The preferred method for separating the organic phase from the second phase containing non-organic meconium solids and other materials is by centrifugation. In accordance with this invention, the separation is performed by centrifuging at high speed sufficient to provide greater than or equal to about 2,500 g of separation force for a period of from about 5 to 15 minutes, preferably 10 minutes until separation is substantially complete. After centrifugation, the top organic acetone phase is transferred into a silanized concentration cup, leaving behind the second phase containing the meconium solids. In accordance with a specially preferred method, the supernatant fluid portion of the centrifuged sample is carefully decanted through a polypropylene frit into the concentration cup to insure removal of solids and large particulates. A polypropylene frit is used because it does not absorb sample and is substantially non-reactive with the sample and sample analyte.

Before evaporating the concentrated extract to further concentrate the meconium group or cocktail extract, a small amount of a sulfating agent is preferably added to convert certain volatile amphetamine analytes to a non-volatile sulfate form to thereby prevent or avoid their becoming entrained with the evaporating volatile solvents. A preferred sulfating agent is a 0.1% sulfuric acid solution in methanol.

In accordance with this aspect of the present method, the volume of the extract is further concentrated from about 6 to 10 ml. down to 0.3 to 0.6 ml. by heating the volatile extract in a sample concentrator at elevated temperatures at or above room temperatures and at pressures at or below atmospheric pressure. Preferably, the sample is concentrated at 75° C. over air and vacuum. The sample concentrator may be commercially obtained from Alltech Corporation, Deerfield, Ill. and an Alltech Model 190-A sample concentrator is especially preferred. A major advantage of the substantially non-aqueous, nondiluted extraction method provided by the volatile organic components is that significant concentration of the sample target analyte may be accomplished rapidly and easily in a commercially available sample concentrator within a period of less than 3 hours and preferably in less than about one and one-half hours. This rapid concentration provided by the volatile organic components renders the preferred extraction method of the invention readily adaptable for commercial laboratory applications.

After the sample has been concentrated to about one-half a milliliter in volume, a portion of the sample is preferably reconstituted in a ratio from about 0.1:1 to about 1:1 with a 50/50 methanol $AD_x$ phosphate buffer solution to provide a stabilized, buffered concentrated extract. The buffered extract concentrate may be directly tested in commercially available fluorescence polarization immunoassay equipment such as the preferred ABBOTT $AD_x$® analyzer instrument available from Abbott Laboratories. In accordance with an especially preferred aspect of the current method, the concentrated buffered extract will be further treated to remove lipids and neutral fats contained therein prior to FPIA screening. The lipids were needed to transfer all target analyte from the meconium into the extract but after target analytes are separated therefrom, the residual lipids if left in the buffered extract tend to interfere with subsequent immunoassay screening procedures. In accordance with this aspect of the method the neutral fats, fatty acids and triglycerides may be removed from the buffered concentrated extract by transferring the buffered extract to a 1.5 ml. micro-centrifuge tube and thereafter centrifuging at high speed for the time sufficient to separate an organic fatty layer from a buffered target analyte concentrate. Thereafter, the fatty lipid layer may be removed by any suitable method including careful aspiration being careful not to remove buffered extract. The remaining de-lipidized or clarified buffered meconium extract concentrate, prepared in accordance with the new and improved method herein, is thereafter analyzed for cocaine metabolite (benzoylecgonine), phencyclidines (PCP), opiates, amphetamines or cannabinoid metabolites using fluorescence polarization immunoassay methods on Abbott's $AD_x$ analyzer, in a manner more particularly to be set forth in the Examples.

In accordance with an important feature of the preliminary immunoassay screening, it has been found in practice that the internal controls and calibrators used to determine heroin, morphine or codeine use during pregnancy should employ free-morphine and codeine forms of the drug as the internal controls, rather than any metabolite form such as a glucuronide form. This finding is based on the discovery that when morphine screening procedures were run, assaying for glucuronide forms and free drug forms in fetal meconium, at least about 90% of the opiate drugs were present in the free drug form rather than in the glucuronide or metabolized form. Prior art methods which assayed for opiates such as morphine and codeine assumed that the drug was present in the glucuronide form. The prior methods included an enzyme hydrolysis step or a high-temperature acid hydrolysis step to convert target analyte prior to assay, and glucuronide forms of the drugs were used as the spiked controls. Applicant has discovered that the prior art methods were using the wrong comparative standards as internal controls. In accordance with this finding, a major time-consuming and expensive hydrolysis step may now be avoided. In accordance with this preferred embodiment of the method, an assay for opiates is performed employing as the internal control standards, free morphine and free codeine drugs to provide an improved immunoassay.

The new and improved preliminary screening extraction and immunoassay methods in accordance with the preferred embodiment of the present invention provides to improved sensitivity and detection of target analytes in meconium samples compared with prior art methods including an aqueous acid extraction steps. The volatile organic extraction methods of this invention when compared to the prior art aqueous acid or methanol extraction procedure, such as that taught by Ostrea et al., showed more than ten-fold improvement in detection sensitivity for the new and improved extraction method of this invention. In an assay screen for opiates employing free drug as the internal controls and using an FPIA immunoassay procedure in accordance with the method of this invention, a screening cut-off concentration or lower limit of opiate detection in the meconium sample was 50 nanograms of opiate per gram of meconium tested. The corresponding lower detection limit for the Ostrea Jr. method for detecting opiates by screening immunoassay was 600 nanograms per gram. Moreover, the preliminary screening cut-off values for detecting phencyclidine (PCP) target analytes was 50 nanograms per gram in accordance with the present method, as compared to a 250 nanograms per gram cutoff employing the Ostrea prior art method. For cannabinoid metabolites, the lower detection limit of the current invention pre-screening assay was 50 nanograms per gram, whereas the Ostrea Jr. method for cannabinoid metabolites had a lower detection sensitivity of 500 nanograms per gram. For cocaine metabolite (benzoylecgonine), the lower limit of detection for the preliminary extraction and screening method in accordance with this invention was 100 nanograms per gram of meconium tested, as compared with 500 nanograms per gram in the Ostrea Jr. prior art. Similarly, a preliminary screening procedure in accordance with the preferred methods of this invention was able to detect amphetamines in the patient samples at concentrations as low as 250 nanograms per gram, whereas the Ostrea Jr. closest prior art methods had a lower detection limit of 1,000 nanograms per gram.

In accordance with this invention preliminary screening extraction and immunoassay methods are described for quickly and rapidly identifying those neonatal patients whose meconium samples indicate have been gestationally exposed to addictive drugs in utero.

In accordance with the method of this invention, once the preliminary screening immunoassay has determined that a sample qualitatively contains a target analyte being assayed for, whether the target analyte be a drug of abuse or its metabolite, or whether it be some other chemical agent of interest, another aliquot portion of that sample is subjected to a more precise GC/MS confirmatory procedure to unequivocally identify and quantitate the amount of that specific target analyte present in that meconium sample in forensically acceptable terms.

In general terms, the GC/MS confirmatory procedures instead of employing a group extraction approach provide a specific extraction known to be the best extraction procedure for that particular target analyte. The second aliquot portion of pre-processed meconium is selected as a starting material for the GC/MS confirmatory for a particular analyte. The test sample is spiked with known quantities of labelled analyte analog. The labelled analyte analogs are preferably deuterated forms of the same drug which by virtue of their isotopic deuterated form have a slightly different and identifiable ionic weight in the GC/MS procedure. The spiked sample containing added internal controls in known quantities together with the unknown quantity of target analyte are thereafter extracted by a specific procedure known to be the most effective for that particular analyte to provide an extract fluid. That extract fluid is separated from meconium solids and purified in a specific procedure to provide a new test fluid containing the spiked internal control sample. This purified fluid is then derivatized with a trimethylsilyl reagent or a heptafluorobutyration reagent to derivatize the spiked internal controls and sample analytes to machine identifiable derivative form. Analysis of the derivatized fluid is performed in GC/MS equipment using electron impact and selected ion monitoring mode.

As has been mentioned above, the particular GC/MS confirmatory assay is specific to a given target analyte. More particularly, the confirmatory GC/MS for cocaine metabolite, benzoylecgonine, improves upon the Rosenzweig method mentioned above by starting with a pre-processed meconium starting material to provide an improved time-averaged aliquot sample. The cocaine confirmatory procedure employs the volatile organic acid and volatile organic solvent co-extraction procedure outlined for the "cocktail" extract to maximize recovery of benzoylecgonine target analyte and the spiked deuterated internal working standards together with some neutral lipid components from the meconium aliquot sample. After the acetic acid/acetone extraction reagents are added, a two-phase mixture is formed and vortexed. The contacted two-phase solution is centrifuged at high speed to separate the organic layer from the second layer. The resulting concentrated non-aqueous meconium extract prepared is reduced in volume in a sample evaporator to 0.5 ml. Thereafter, the concentrated analyte analogs and target analytes for cocaine are reconstituted in a half a milliliter of ethanol and 6 ml. of a phosphate buffer at a pH of 6. This mixture is vortexed thoroughly and centrifuged at high speed until a top lipid layer is formed. The top lipid layer is separated from the lower buffered extract layer by careful aspiration. To this point in the extraction procedure, an improved recovery over the Rosenzweig method is accomplished by using the more efficient acetic acid/acetone extraction to recover target analyte still dissolved in the fatty components of the meconium. After separating the target analytes and the unwanted fats together as a unit, the volatiles are driven off in a concentration step. Reconstituting with methanol provides a selective solvent for the cocaine target analytes and analyte analogs in which the fats are not particularly soluble. The addition of the phosphate buffer followed by centrifuging now separates the enhanced recovery of the desired target analytes and analogs, and from the undesired lipid components. This effectively increases the total amount of target analyte recovered from the meconium sample than would be obtained from following the Rosenzweig method of extracting with methanol alone, as the first step.

The clarified lipid-free buffered extract is subjected to solid phase extraction using a BOND ELUTE CERTIFY brand (VARIAN) solid phase extraction column by sequentially passing through each column, methanol, phosphate buffer at pH 6 and sample. After rinsing, selectively extracted target analytes and analyte analogs are eluted with a polar organic solvent containing ammonium hydroxide. The resulting eluate is taken to dryness in a sample concentrator and reconstituted in alcohols. Thereafter the trimethylsilyl derivative is made by incubating the eluted target analytes with the trimethylsilyl derivatizing agent with heating for a time sufficient until derivatization is complete. Thereafter, the derivatized sample is injected into the gas chromatograph/mass spectrometer.

The amount of cocaine metabolite target analyte present in the meconium sample is calculated based on a comparison of the native cocaine and benzoylecgonine sample response to the known response of the quantitatively known deuterated cocaine and benzoylecgonine analogs. The ratio of the target analyte area versus the labelled analog area is determined and this ratio is multiplied by the amount of labelled analog added to the extract divided by the mass of the meconium sample tested. The resulting calculation expresses the quantity of cocaine and/or cocaine metabolite present in the original sample in terms of nanograms of cocaine or metabolite per gram of meconium tested.

The new and improved GC/MS confirmatory assay for cocaine and its metabolite, benzoylecgonine, in accordance with this invention is able to detect analyte concentrations greater than or equal to 25 nanograms per gram. The closest prior art confirmation has a corresponding lower detection sensitivity or limit of 250 nanograms per gram. The new and improved cocaine confirmatory procedure of this invention exhibited a tenfold improvement in detection sensitivity over the prior art.

In accordance with the present invention, heretofore unavailable GC/MS confirmatory methods for quantifying the amount of opiate analytes, amphetamine analytes, tetrahydrocannabinoid metabolite analytes and phencyclidine analytes in neonatal meconium samples are now provided. In accordance with these new confirmatory procedures for opiates and for amphetamines, each employ a specialized liquid/liquid extraction technique is employed for each target analyte. In the opiate confirmation assay, a sample of pre-processed meconium is spiked with known quantities of deuterated codeine and morphine analogs as internal standard controls. Thereafter, the spiked meconium sample is extracted by homogenizing in concentrated hydrochloric acid to release target analytes from the meconium matrix. After being homogenized and centrifuged, the top aqueous acid layer is transferred to a silanized, capped glass tube to provide a first aqueous acid extract. In the opiate confirmation assay, the first acid extract is extracted with methyl-t-butyl ether to remove lipids and the top organic layer is carefully aspirated and discarded. The clarified acid layer is neutralized with base and then back extracted into an organic ether solvent and buffered. The buffered extract is centrifuged and the top organic phase is removed to provide a final opiate extract for concentration in a sample concentrator. The samples are taken to dryness in the sample concentrator, reconstituted in ethanol, transferred to auto-sampler vials and taken to dryness at elevated temperature and reduced pressure. The target analytes and opiate analogs present in the dried auto-sampler vial are derivatized by vapor phase derivatization with a N-methyl-N-trimethylsilyltrifluoroacetamide derivatizing agent. Thereafter the GC/MS spectra is taken in selective ion mode. The quantity of opiates in the form of morphine or codeine present in the original meconium sample is determined by comparing the native opiate drug response against the response of the quantitatively known deuterated analogs. A ratio of the native drug area versus the labelled analog area in the extract multiplied by the concentration of the labelled analyte in the extracted mass yields a final quantitative measurement of opiate concentration in terms of nanograms of opiate per gram of meconium tested.

In the amphetamine confirmation assay a sample of pre-processed meconium is spiked with working internal standards of d-amphetamine-d5 and methamphetamine-d8 to provide a spiked meconium sample. The spiked sample is extracted with concentrated hydrochloric acid with homogenization followed by centrifugation to define a top aqueous acid layer. The aqueous acid layer extract is also transferred to a silanized glass tube for further processing. In the amphetamine confirmation, the first acid extract is neutralized with base, buffered and extracted in a mixed organic solvent extraction into a top organic solvent phase. The top organic phase is transferred to a clean tube, re-acidified with hydrochloric acid and centrifuged to define a top organic phase and a lower aqueous acid phase containing target analyte and spiked amphetamine analogs. Once again, the acid extract solution is neutralized, buffered and back extracted with an organic solvent to collect the amphetamine target analyte and analog values into the organic phase. After centrifugation and separation, the top organic phase is transferred to an aluminum concentrator vial, treated with a sulfating agent and taken to dryness with heat and forced air. The sample analytes are reconstituted in ethyl alcohol, transferred to an auto-sampler vial and again taken to dryness at elevated temperature and reduced pressure. The target analytes are reconstituted in an organic hydrocarbon solvent and derivatized with an N-methylbis(heptafluorobutyramide) derivatizing agent. The derivatized solution is run through the GC/MS in selective ion monitoring mode. The amount of amphetamines contained in the original meconium product is determined by comparing the native amphetamine response against the response of the spiked amphetamine analogs. The ratio of native drug area versus the labelled analog area times the analog concentration in the extracted mass yields a final quantitative determination of amphetamine present in terms of nanograms of amphetamine per gram of meconium sample tested.

The new and improved confirmatory procedure for quantitatively determining the amount of marijuana metabolite found in a meconium sample comprises a selected assay for 11-nor-delta-9-tetrahydrocannabinol-9-carboxylic acid (the delta-9-carboxy-THC or glucuronide metabolite). In accordance with this procedure, the deuterated glucuronide metabolite is spiked into a sample of pre-processed meconium. In practice, it has been shown that acetic acid/acetone extraction for the glucuronide metabolite of marijuana is not as efficient an extraction agent as absolute methanol. Accordingly, for this marijuana metabolite confirmatory assay, methanol is used as the extraction solvent. After spiking and adding methanol, the sample is homogenized for a time period and allowed to rest for five minutes. A concentrated base in the form of sodium or potassium hydroxide is added and the mixture is vortexed. The vortexed mixture is thereafter centrifuged and the top phase is transferred to a clean, silanized glass tube. The top phase is diluted with deionized water and an extraction solvent including ethyl acetate and N-hexane. The second mixture is vortexed and permitted to incubate for 15 minutes. The top organic phase is aspirated and discarded. Concentrated HCL is added to each tube and vortexed to convert the target analytes and analyte analogs to their organic soluble form. A fresh organic extraction solvent is added to the tube to form a two-phase extraction mixture. After thorough mixing and separation by centrifuge, the top organic phase is transferred to concentration cups. The purified organic extracts are taken to dryness in a sample concentrator at elevated temperature and reduced pressure. After reconstituting in alcohol and being transferred to auto-sampler vials, the samples are again taken to dryness at elevated temperature in a vacuum. Thereafter, the target analytes and analogs are derivatized with a N-methyl-N-trimethylsilyltrifluoroacetamide derivatizing agent. Thereafter, the derivatized sample is injected into the GC/MS and selected ions are monitored. The results are determined by comparing the native drug response to the quantitatively known deuterated analog spiked into the sample. The quantitative calculation is made by multiplying the ratio of the native marijuana metabolite area found versus the area of the deuterated marijuana metabolite analogs. That ratio is then multiplied by the amount of labelled analog in the extract and divided by the extract mass to provide a final determination expressed in terms of nanograms of marijuana metabolite present per gram of meconium tested.

In accordance with still another alternate aspect, the present invention provides a new and improved forensically-acceptable GC/MS confirmatory procedure for unequivocally identifying and quantifying the presence of phencyclidine (PCP) analytes in neonatal meconium samples to prove maternal use of PCP during pregnancy. More particularly, the PCP confirmation method of this invention first includes the step of spiking a known amount of deuterated PCP analog into a known quantity of pre-processed meconium to form a spiked sample. The spiked sample is homogenized with glacial acetic acid until a substantially uniform homogenate is obtained. Acetone and diphenylamine are added to form a two-phase mixture which is vortexed then centrifuged to define a top organic phase and a second phase. The top organic is transferred to a silanized concentration cup and a minor amount of alcoholic sulfuric acid is added to prevent target analyte from entraining with evaporating volatile organic solvents. The transferred organic phase containing target analytes and analyte analogs is concentrated at elevated temperature and with reduced pressure until the volume approaches about 0.5 ml. The concentrated analyte phase is reconstituted in methanol and transferred to a polypropylene tube. The reconstituted concentrate is buffered, vortexed and centrifuged. Any top lipid layer is carefully removed by aspiration and discarded. The remaining clarified and buffered extract is passed through a BOND ELUTE CERTIFY brand solid phase extraction column. After column rinsing, the phencyclidine target analytes and deuterated analyte analogs are eluted with ammonium hydroxide and ethyl acetate. The eluate is placed in an aluminum concentration vial and evaporated to dryness.

The residue is thereafter reconstituted with a mixed Isooctane/isopropanol (80/20) solvent and carefully transferred to auto-sampler vials containing 250 microliter volume inserts. The sample is injected into the GC/MS instrument and read. The amount of phencyclidine present is determined by comparing the ratio of the response area for sample analyte to the area of the response for the spiked analyte analog. Thereafter, the response ratio is multiplied by the amount of known spiked internal control over the mass of the sample to provide the quantity of phencyclidine present in the meconium sample in terms of nanograms of phencyclidine per gram of meconium tested.

Further details and advantages provided by the present invention, in all its aspects, will become apparent from the following examples.

DESCRIPTION OF THE PREFERRED EMBODIMENTS

PREPARATION A—SILANIZATION OF GLASSWARE

Glass, by its chemical nature, has a very active surface that contains many free hydroxyl groups. One of the disadvantageous characteristics of laboratory glassware is the ability of the glass surfaces to bind organic compounds such as drug analytes and their metabolites. To overcome this error-introducing problem, the glass surfaces may be deactivated by the formation of silyl ethers with the free surface hydroxyl groups. This is accomplished in the vapor phase by reacting the glass surfaces with dimethyldichlorosilane (DMCS). In accordance with the preferred embodiment of this invention, all glassware which comes in contact with the various samples and sample extracts and solutions will be silanized in accordance with the following procedure.

In accordance with this preparatory method, glassware to be used and treated is placed in an appropriate rack. A 2 ml vial containing at least about 1 ml of dimethyldichlorosilane (DMCS) is placed into a vacuum oven set at elevated temperatures of between about 75° to 85° C. The rack and glassware are placed into the vacuum oven and the door is tightly closed. The vacuum valve is opened to initiate vacuum in the oven. When the vacuum gauge indicates an internal oven pressure of less than or equal to 25 inches of mercury, the vacuum valve is closed. The glassware is permitted to react with the silanizing agent vapors for at least about 15 minutes. Thereafter, the vacuum valve is opened and the DMCS vapors are exhausted from the vacuum oven. The glassware is removed from the oven and allowed to cool to room temperature. All of the treated glassware is thereafter rinsed in clean reagent grade acetone. After rinsing, the glassware is permitted to thoroughly dry prior to use.

The silanized treated glassware should be clear of any signs of contamination and feels slightly slippery to the touch. Any glassware that is discolored or smudged or which lacks a slippery feel to the touch should not be used.

PREPARATION B—PRE-PROCESSING OF THE POOLED MECONIUM SAMPLE

A meconium sample is prepared for extraction and testing by collecting each of the meconium bowel movements produced by a neonatal infant in the immediate postpartum period in a polyethylene-lined diaper. The meconium retained on the polyethylene liner sheet placed in each diaper is transferred to a polypropylene sample container equipped with a screw-on lid. Between collections, the pooled sample is kept under refrigeration until sample collection is substantially complete, e.g., typically after the first two to three days of the neonate's life. The meconium excreta is collected and pooled until the first appearance of the transitional stool is observed. Transitional stool is not included in the sample specimen.

When sample collection is substantially complete, the pooled meconium excreta is pre-processed by introducing a flat bladed instrument, such as a wooden spatula, into the sample vial and vigorously mashing and mixing the meconium matrix in an effort to remove obvious striations present in the meconium tissue samples and to achieve a redistribution of the target analytes within all of the collected meconium. The effort is to try and achieve a smoothed, substantially uniform, pre-processed product so that the aliquot portions taken from the pre-processed product will exhibit low sample to sample variability. The meconium tissue is extremely rubbery and resists being smoothed. However, improved reproducibility and accuracy for the testing requires that the preprocessing be as thorough, complete and effective as possible. In any event, some pre-stirring pre-processing is certainly better than none and vigorous stirring, mashing and mixing for a period of from 1 to 5 minutes with the bladed spatula is generally effective to create the smooth, evenly-distributed product.

EXAMPLE 1

METHOD FOR MAKING CONCENTRATED COCKTAIL MECONIUM EXTRACT FOR PRELIMINARY SCREENING BY FLUORESCENCE POLARIZATION IMMUNOASSAY METHODS

A non-aqueous, substantially non-diluted, concentrated volatile organic cocktail extract was prepared as follows:

A number of reagent solutions were prepared prior to performing the extraction. A volatile organic solvent including a minor effective amount of a glass anti-binding agent was prepared by weighing 6.68 milligrams of diphenylamine and adding it to a fresh 4 liter bottle of reagent grade acetone. After thorough mixing, the 1.67 mg/l diphenylamine in acetone solution was labelled.

A stable buffer comprising a 50/50 volume/volume mixture of ABBOTT $AD_x$® buffer in absolute methanol was prepared by mixing equal portions of the $AD_x$ buffer and methanol together in a suitably sized container. The $AD_x$ buffer/MeOH reagent solution was labelled appropriately.

A 0.1% $H_2SO_4$ in MeOH solution was prepared by pipetting 100 microliters of concentrated sulfuric acid into 100 milliliters of absolute methanol. The alcoholic sulfuric acid solution was labelled appropriately and stored for a period of up to one month.

After preparation of the reagents, the new and improved cocktail extract method was performed in accordance with this invention as follows:

A 1.0 gram sample of the pre-processed neonatal meconium obtained in Preparation B set forth above was placed in a 16 by 125 polypropylene tube. 3.0 mls. of reagent grade glacial acetic acid was added to the polypropylene tube and sample. The volatile organic acid and pre-processed meconium were homogenized using an OMNI 5000 tissue homogenizer set at the highest speed for a period of at least about 15 seconds until a smooth, substantially uniform finely-divided homogenate was formed. The homogenate after the tissue homogenizing treatment had an average particle size of between about 2 to about 5 microns. After homogenization, 6.0 mls. of the acetone/diphenylamine reagent solution was added to the sample tube. The resulting mixture was vortexed and allowed to mix in a sample mixer for more than 5 minutes. The resulting two-phase mixture including an organic phase and a second phase including the meconium solids and other materials is separated by centrifuging at high speed for a period of about 10 minutes. The top organic acetone phase is decanted through a 30 micron polypropylene frit and added to a silanized concentration cup. A drop of the 0.1% $H_2SO_4$ in methanol solution was added to each cup, to prevent loss of amphetamine analyte due to co-evaporation with entrained solvents. The resulting organic extract was concentrated to a volume of less than 0.5 ml. in an Alltech sample concentrator, Model 190-A set at 75° C. over air and vacuum. The resulting concentrated sample appeared to have a top lipid layer with little or no sample volume thereunder. After concentration, the target analytes are reconstituted with 0.7 ml. of the $AD_x$ buffer/MeOH reagent. In accordance with a preferred feature of this invention, the interfering fats and lipid phases are removed from the reconstituted buffered extract by transferring the reconstituted extract to a 1.5 ml. microcentrifuge tube and centrifuged at high speed for a period of at least about 5 minutes. The top organic lipid layer was carefully aspirated and removed to provide a clarified, concentrated and buffered meconium extract for further testing.

EXAMPLE 2

QUALITATIVE PRELIMINARY SCREENING PROCEDURE FOR COCAINE METABOLITE

An aliquot portion of the clarified, buffered meconium extract concentrate prepared in accordance with the method of Example 1 was evaluated for the presence of cocaine metabolite (benzoylecgonine) by a commercially available fluorescence polarization immunoassay (FPIA) method on commercially available ABBOTT $AD_x$® analyzer equipment, employing the $AD_x$ instrument, its protocols and ABBOTT $AD_x$® reagents.

The FPIA cocaine metabolite assay is a homogeneous fluorescence polarization immunoassay designed to detect the cocaine metabolite benzoylecgonine in biological specimens. The assay is based on competition between any cocaine metabolite present in the sample and benzoylecgonine labelled with fluorescein for a limited number of antibody binding sites. Fluorescence polarization decreases upon binding of the fluorescein labelled benzoylecgonine to the antibody, and the amount that is bound is inversely related to the benzoylecgonine concentration in the sample. Thus, in accordance with the instrumental method, fluorescence polarization decreases directly with benzoylecgonine concentration present in the sample. The degree of fluorescence polarization is measured by a liquid crystal in the instrument and the concentration of immuno-reactive benzoylecgonine equivalence is determined on the ABBOTT $AD_x$® analyzer comparing the instrument value of the unknown with a standard curve derived from the instrument values of known calibrators and internal controls.

An ABBOTT $AD_x$® cocaine metabolite assay kit (ABBOTT Catalog Number 9670–77) is equipped with a number of assay reagents and a number of calibrators comprising human urine spiked with benzoylecgonine at certain known concentrations. For purposes of this new and improved meconium assay procedure certain negative control solutions are prepared in preparation for performing the FPIA immunoassay. A Lyphocheck screen control containing 375 nanograms per milliliter of benzoylecgonine was obtained from BIO-RAD, INC. under their Catalog Number 476 in 10, 10 ml. samples. The unopened bottles were stored at 2° to 8° C. prior to use. Before performing the assay, the screen controls from BIO-RAD were permitted to equilibrate to room temperature. The control solution was swirled to insure homogeneity being careful to avoid foaming.

A negative control sample was obtained from UNITED STATES DRUG TESTING LABORATORIES. The negative control samples were prepared in 500 ml. bottles and are certified to be drug-free. These negative control samples are stored under refrigeration at 2° to 8° C. when not in use. The negative controls obtained from USDTL were not used and discarded if bacterial contamination or turbidity was evidence upon visual inspection.

Negative meconium controls were prepared by weighing 1 gram samples of drug-free meconium and performing the extraction procedure set forth in Example 1 to provide the negative control fluid for use in the FPIA assay.

Positive meconium controls were prepared by taking 1 gram samples of drug-free meconium and pipetting 100 microliters each of a spiking solution having a benzoylecgonine concentration of 4,000 nanograms per ml. and a cocaine control spiking solution containing 2,000 nanograms per ml. of cocaine, respectively.

After preparation of all the calibrators and controls and equilibration to room temperature was substantially completed, a 100 microliter sample of the cocktail extract solution obtained in accordance with the method of Example 1 is employed as the sample unknown for FPIA analysis for the presence of cocaine metabolites in the original meconium sample. The FPIA immunoassay sample was run in accordance with standard ABBOTT $AD_x$® procedures. The instrument values were recorded. A meconium extract sample unknown that gives an instrument derived value greater than the stored threshold value (in part determined by the negative controls) was recorded as a positive finding for cocaine metabolite in that sample.

Repeated experiments against known positive control specimens employing the methods of Examples 1 and 2 has revealed that the qualitative FPIA preliminary screening assay in accordance with this invention for cocaine metabolite is capable of providing reproducibly accurate positive determinations of the presence of cocaine metabolite at concentrations of benzoylecgonine as low as 15 nanograms per gram of meconium sample tested.

EXAMPLE 3

QUALITATIVE PRELIMINARY SCREENING PROCEDURE FOR AMPHETAMINE CLASS ANALYTES

An aliquot portion of the clarified buffered meconium extract concentrate prepared in accordance with the method of Example 1 was evaluated for the presence of d-amphetamine or methamphetamine by an ABBOTT $AD_x$® FPIA immunoassay in a manner similar to the method of Example 2. The FPIA amphetamine class analytes assay is a homogeneous fluorescence polarization immunoassay designed to detect d,1-amphetamine, d-amphetamine and methamphetamine in biological specimens. Other structurally similar phenethylamines can also produce positive results. The assay is based on competition between any amphetamines present in the sample and amphetamine labelled with fluorescein for a limited number of antibody binding sites. Fluorescence polarization decreases upon binding of the fluorescein labelled amphetamine to the antibody, and the amount that is bound is inversely related to the amphetamine concentration in the sample. Accordingly, fluorescence polarization decreases directly with amphetamine concentration. The degree of fluorescence polarization is measured by a liquid crystal in the instrument and the concentration of the immunoreactive amphetamine equivalents is determined on the ABBOTT $AD_x$® analyzer by comparing the instrument value of the amphetamine target unknowns with a standard curve derived from the instrument values of known calibrators and internal controls.

An ABBOTT $AD_x$® amphetamines class assay kit (ABBOTT Catalog Number 1A99-77) is equipped with a number of assay reagents and a number of calibrators comprising human urine spiked with d-amphetamine at certain known concentration. For purposes of this new and improved meconium assay procedure, certain negative control solutions are prepared in preparation for performing the FPIA assay. A Lyphocheck screen control containing 1,250 ng/ml. amphetamine was obtained from BIO-RAD, INC., under their Catalog Number 476 in 10, 10 ml. vials. The unopened bottles are stored at 2° to 8° C. prior to use. Before performing the assay, the screen controls from BIORAD are permitted to equilibrate to room temperature. The BIO-RAD control solutions are swirled to insure homogeneity with care being taken to avoid foaming.

A negative control sample was obtained from UNITED STATES DRUG TESTING LABORATORIES. The negative control samples were prepared in 500 ml. bottles and were certified to comprise drug-free human urine. These negative control samples were stored under refrigeration at 2° to 8° C. when not in use. The negative controls obtained from USDTL were not used, but were discarded if bacterial contamination or turbidity was evident upon visual inspection.

A negative meconium control sample was prepared by weighing a 1.0 gram sample of drug-free meconium and performing the extraction procedure as set forth in Example 1 to provide the negative control fluid extract for use in the FPIA assay.

Positive meconium controls were prepared by spiking 1.0 gram samples of drug-free meconium with 100 microliter aliquots of spiking solutions containing 1,000 ng/ml amphetamine and 1,000 ng/ml. methamphetamine, respectively.

After preparation of all the calibrators and controls and equilibration to room temperature, a 100 microliter sample of the cocktail extract solution obtained in accordance with the method of Example 1, is employed as the sample unknown for FPIA analysis for the presence of amphetamine in the original meconium sample. The FPIA immunoassay sample was run in accordance with standard ABBOTT $AD_x$® procedures. The instrument values were recorded. A meconium extract sample unknown giving an instrument derived value greater than the stored threshold values (in part determined by the negative controls) was recorded as a positive finding for amphetamine in that sample.

Repeated experiments against known positive control specimens employing the methods of Examples 1 and 3 herein has revealed that the qualitative FPIA preliminary screening assay in accordance with this invention for amphetamine is capable of providing reproducibly accurate positive determinations of the presence of amphetamine at concentrations of amphetamine or methamphetamine as low as 250 ng/g of sample meconium tested.

EXAMPLE 4

QUALITATIVE PRELIMINARY SCREENING PROCEDURE FOR OPIATE ANALYTES

An aliquot portion of the clarified, buffered meconium extract concentrate prepared in accordance with the method of Example 1 was evaluated for the presence of morphine and codeine by an ABBOTT $AD_x$® FPIA immunoassay in a manner similar to the method described in Examples 2 and 3. The FPIA opiate assay is a homogeneous fluorescence polarization immunoassay designed to detect morphine and codeine in biological specimens. Other structurally similar opiates can also produce positive results. The assay is based on competition between any opiates present in the sample and morphine labelled with fluorescein for a limited number of antibody binding sites. Fluorescence polarization decreases upon binding of the fluorescein labelled morphine to the antibody, and the amount that is bound is inversely related to the morphine concentration in the sample. Thus, fluorescence polarization decreases directly with morphine concentration. The degree of fluorescence polarization is measured by a liquid crystal and the concentration of immunoreactive morphine equivalents is determined on the ABBOTT $AD_x$® analyzer comparing the instrument value of the unknown against a standard curve derived from the instrument values of known calibrators and internal controls.

An ABBOTT $AD_x$® opiate assay kit (ABBOTT Catalog Number 9673-77) is equipped with a number of assay reagents and spiked human urine calibrators including known quantities of morphine. For purposes of this new and improved meconium assay procedure, certain negative control solutions were prepared in preparation before performing the FPIA immunoassay. A Lyphocheck screen control solution containing 375 ng/ml. of morphine obtained from BIO-RAD, INC. under their Catalog Number 476 in 10 ml. vials were kept in stored unopened bottles under refrigeration until ready for use. Immediately before use the known control samples were permitted to equilibrate to room temperature and gently swirled to insure homogeneity.

A negative control sample comprising drug-free urine was obtained from the UNITED STATES DRUG TESTING LABORATORIES. A negative meconium control was prepared by weighing a 1.0 gram sample of certified drug-free meconium and subjecting that sample to the extraction procedure set forth in Example 1 to provide a negative control fluid for use in the FPIA assay. Positive meconium controls were prepared by taking 1.0 gram samples of drug-free meconium and spiking them with 100 microliters of a spiking solution containing 1,000 ng/ml. of morphine and codeine, respectively. After preparation of all calibrators and controls, all test solutions were permitted to come to room temperature and a 100 microliter sample of the cocktail extract solution obtained in accordance with the method of Example 1 was employed as the sample unknown for FPIA analysis for the presence of opiates in the original meconium sample. The FPIA immunoassay sample was run in accordance with standard ABBOTT $AD_x$® protocols in accordance with the method described in Examples 2 and 3.

Repeated experiments against known positive control specimens employing the method of Example 4 has revealed that the qualitative FPIA preliminary screening assay in accordance with this invention for opiates is capable of providing reproducibly accurate positive determinations of the presence of opiate analytes at concentrations of morphine or codeine as low as 50 ng/g of meconium sample tested.

EXAMPLE 5

QUALITATIVE PRELIMINARY SCREENING PROCEDURE FOR CANNABINOID ANALYTES

An aliquot portion of the clarified, buffered meconium extract concentrate prepared in accordance with the method of Example 1, was evaluated for the presence of marijuana metabolites by an ABBOTT $AD_x$® FPIA immunoassay in accordance with the methods of Examples 2–4.

The cannabinoid delta-9-tetrahydrocannabinol-(delta$^9$-THC) is the principle psychoactive ingredient marijuana and hash-hish. The compound delta$^9$-THC is quickly and effectively absorbed by inhalation or from the gastrointestinal tract and is almost completely metabolized. Excretion of urinary metabolites begins within hours after exposure to cannabinoids. The prevalent theory is that delta$^9$-THC is distributed in and absorbed by various fatty tissues and then is very slowly released to the plasma. Thereafter, it is readily metabolized in the liver and eventually excreted in the urine and feces. The ABBOTT fluorescence polarization cannabinoid assay detects the major metabolite of delta$^9$-THC, i.e., 11-nor-delta$^9$-THC-9-carboxylic acid. It also detects other delta$^9$-THC metabolites.

The FPIA assay is a homogeneous fluorescence polarization immunoassay technique used for the analysis and detection of cannabinoid metabolite compounds in biological fluids. As with the other ABBOTT $AD_x$® assays, the assay is based on competition between drug metabolites present in the sample and known quantities of fluorescein labelled drug metabolite analogs added to the sample specimen which compete for a known quantity of antibody binding sites.

For this marijuana metabolite assay the ABBOTT $AD_x$® cannabinoids assay kit (ABBOTT Catalog Number 9671-77) was employed. In addition to the standard cannabinoid assay reagents provided with the ABBOTT kit, a number of internal open controls were prepared especially in accordance with the methods of the invention. More particularly, a Lyphocheck screen control containing 125 ng/ml. of cannabinoid was obtained from BIO-RAD, INC. under their Catalog Number 476 in a quantity of 10, 10 ml. vials. A negative control of drug-free urine was obtained from UNITED STATES DRUG TESTING LABORATORIES in 500 ml. bottles.

Negative meconium controls were also prepared by extracting 1.0 gram samples of known drug-free meconium in accordance with the extraction method set forth in Example 1. Positive meconium controls were prepared by spiking 1.0 gram samples of drug-free meconium with 100 microliter aliquot of a solution containing 580 ng/ml. of THC-COOH glucuronide.

A 100 microliter sample of the cocktail extract solution obtained in accordance with the method of Example 1 was employed as the sample unknown for the FPIA analysis for the presence of marijuana metabolite in the original meconium sample. The FPIA immunoassay was run in accordance with standard ABBOTT $AD_x$® protocols. The instrument values were recorded and any instrument values greater than stored threshold values were recorded as a positive finding for marijuana metabolites in the sample.

Repeated experiments against known positive control specimens employing the methods of Examples 1 and 5 has revealed that the qualitative FPIA preliminary screening assay in accordance with this invention for marijuana metabolite is capable of providing reproducibly accurate positive determinations of the presence of marijuana metabolite at concentrations of the glucuronide metabolite as low as 50 ng/g of meconium sample tested.

EXAMPLE 6

QUALITATIVE PRELIMINARY SCREENING PROCEDURE FOR PHENCYCLIDINE (PCP) ANALYTES

An aliquot portion of the clarified, buffered meconium extract concentrate prepared in accordance with the method of Example 1 was evaluated for the presence of PCP by an ABBOTT $AD_x$® FPIA immunoassay in a manner similar to the method of Examples 2–5. The FPIA phencyclidine analyte assay is a homogeneous fluorescence polarization immunoassay designed to detect PCP in biological specimens. An ABBOTT $AD_x$® phencyclidine-2 assay (ABBOTT Catalog Number 9672-76) was employed as the reagent and calibration kit for the assay. Additional controls including a Lyphocheck screen control containing 32 ng/ml. of PCP obtained from BIO-RAD, INC. under BIO-RAD Catalog Number 476 in 10 ml. sample vials was obtained. Negative control urine samples from UNITED STATES DRUG TESTING LABORATORIES in 500 ml. bottles was also obtained. Negative meconium control samples comprising 1.0 gram samples of drug-free meconium extracted in accordance with the method of Example 1 to provide a negative meconium control test fluid were also prepared. Positive meconium controls were prepared by spiking 1.0 gram samples of known drug-free meconium with 100 microliters of a PCP solution containing 500 ng/ml. PCP. The FPIA analysis employing a 100 microliter sample of the cocktail extract solution obtained in accordance with the method of Example 1 was run on the analyzer employing standard ABBOTT $AD_x$® procedures.

Repeated experiments against known positive control specimens employing the methods of Examples 1 and 6 has revealed that the qualitative FPIA preliminary screening assay in accordance with this invention for PCP is capable of providing reproducibly accurate positive determinations of the presence of PCP analyte at concentrations of PCP as low as 50 ng/g of meconium tested.

EXAMPLE 7

COMPARATIVE EXTRACTION EFFICIENCIES OF MECONIUM TISSUE SAMPLES BY A VARIETY OF VOLATILE ORGANIC ACIDS

In the following examples, experiments were conducted to determine the most efficient volatile organic reagent system for providing maximum cocktail recovery of the various target analytes from a meconium tissue specimen in a single extraction procedural step. In accordance with this study, six negative drug-free meconium specimens were spiked with known amounts of several target analytes to form a spiked positive control specimens identified as Positive Controls A through F. Each of the spiked positive controls samples A through F were spiked with the following added target analytes:

| TARGET ANALYTE | NG/GRAM |
|---|---|
| THC-COOH GLUCURONIDE | 58 NG/GRAM |
| BENZOYLECGONINE | 400 NG/GRAM |
| COCAINE | 200 NG/GRAM |
| CODEINE | 100 NG/GRAM |
| MORPHINE GLUCURONIDE | 100 NG/GRAM |
| PCP | 50 NG/GRAM |
| AMPHETAMINE | 100 NG/GRAM |
| METHAMPHETAMINE | 100 NG/GRAM |

Each of these spiked positive control specimen samples were extracted in accordance with the general method outlined in Example 1 except that for some aliquot portions of the positive control samples a volatile organic acid selected from acetic acid, propionic acid, trifluoroacetic acid and formic acid were used as the analyte liberating reagents. Thereafter, the volatile organic acetone solvent was added in the extraction protocol of Example 1 and was followed until a clarified, buffered meconium extract concentrate was obtained for each organic acid extracting agent and for each positive control sample. Thereafter, aliquot portions of the clarified, buffered extract concentrates for each acid and each positive control sample were screened in accordance with the screening procedures outlines in Examples 2–6 to make a qualitative determination of the amount of spiked analyte present in the spiked positive control samples A through F. The results obtained for the various volatile organic acid extracting agents for each of these six positive control specimens as determined by the ABBOTT $AD_x$® FPIA protocols is set forth in Table 1 as follows:

TABLE 1

COMPARATIVE EXTRACTION EFFICIENCIES OF VARIOUS ORGANIC ACIDS FOR MECONIUM BOUND TARGET ANALYTES

| | THC | COCN | OPIATES | PCP | AMPS |
|---|---|---|---|---|---|
| ACETIC ACID | | | | | |
| POS CONTROL 1 | 67.7 | 549.0 | 136.0 | 19.3 | 1418.0 |
| POS CONTROL 2 | 66.5 | 584.0 | 147.0 | 29.4 | 1668.0 |
| POS CONTROL 3 | 68.5 | 520.0 | 131.0 | 17.0 | 1884.0 |
| POS CONTROL 4 | 61.7 | 403.0 | 128.0 | 17.9 | 1752.0 |
| POS CONTROL 5 | 59.4 | 970.0 | 119.0 | 22.7 | 1232.0 |
| POS CONTROL 6 | 55.6 | 363.0 | 121.0 | 18.1 | 2010.0 |
| MEAN VALUE | 63.2 | 564.8 | 130.3 | 20.7 | 1660.7 |
| STD DEV | 4.7 | 197.4 | 9.4 | 4.3 | 265.5 |
| PROPIONIC ACID | | | | | |
| POS CONTROL 1 | 64.9 | 307.0 | 103.0 | 12.8 | 1661.0 |
| POS CONTROL 2 | 74.3 | 488.0 | 101.0 | 19.0 | 1577.0 |

TABLE 1-continued

COMPARATIVE EXTRACTION EFFICIENCIES OF VARIOUS ORGANIC ACIDS FOR MECONIUM BOUND TARGET ANALYTES

| | THC | COCN | OPIATES | PCP | AMPS |
|---|---|---|---|---|---|
| POS CONTROL 3 | 59.4 | 564.0 | 111.0 | 42.3 | 1771.0 |
| POS CONTROL 4 | 62.9 | 588.0 | 126.0 | 53.5 | 1514.0 |
| POS CONTROL 5 | 69.2 | 303.0 | 95.0 | 13.8 | 1888.0 |
| POS CONTROL 6 | 77.9 | 369.0 | 98.0 | 31.9 | 1604.0 |
| MEAN VALUE | 68.1 | 436.5 | 105.7 | 28.9 | 1669.2 |
| STD DEV | 6.4 | 116.2 | 10.4 | 15.2 | 125.9 |
| TRIFLUOROACETIC ACID | | | | | |
| POS CONTROL 1 | 0.0 | 0.0 | 70.0 | 0.0 | 1170.0 |
| POS CONTROL 2 | 3.4 | 292.0 | 86.0 | 5.0 | 886.0 |
| POS CONTROL 3 | 0.0 | 72.0 | 95.0 | 0.0 | 1671.0 |
| POS CONTROL 4 | 2.0 | 533.0 | 88.0 | 1.7 | 687.0 |
| POS CONTROL 5 | 10.0 | 351.0 | 83.0 | 10.4 | 951.0 |
| POS CONTROL 6 | 0.0 | 209.0 | 96.0 | 0.0 | 1578.0 |
| MEAN VALUE | 2.6 | 242.8 | 86.3 | 2.9 | 1157.2 |
| STD DEV | 3.6 | 176.8 | 8.7 | 3.8 | 360.2 |
| FORMIC ACID | | | | | |
| POS CONTROL 1 | 18.3 | 453.0 | 133.0 | 25.3 | 1926.0 |
| POS CONTROL 2 | 21.4 | 543.0 | 152.0 | 32.7 | 1345.0 |
| POS CONTROL 3 | 20.3 | 453.0 | 118.0 | 34.4 | 1958.0 |
| POS CONTROL 4 | 23.2 | 571.0 | 147.0 | 30.5 | 1895.0 |
| POS CONTROL 5 | 25.3 | 450.0 | 126.0 | 25.2 | 1948.0 |
| POS CONTROL 6 | 22.1 | 403.0 | 149.0 | 26.2 | 1693.0 |
| MEAN VALUE | 21.8 | 478.8 | 137.5 | 29.1 | 1794.2 |
| STD DEV | 2.2 | 58.5 | 12.7 | 3.7 | 219.9 |

From the data of Table 1 the increasing order of extraction efficiency for the volatile organic acids in combination with the volatile acetone solvent extraction system was trifluoroacetic acid < formic acid < propionic acid < acetic acid.

EXAMPLE 8

GC/MS CONFIRMATION PROCEDURE FOR QUANTITATIVE MECONIUM ANALYSIS FOR COCAINE

In accordance with this invention, neonatal meconium samples testing positive for cocaine metabolite, benzoylecgonine, in the preliminary FPIA immunoassay screening procedures described in Examples 1 and 2, were subjected to a confirmatory quantitative GC/MS analysis to provide a forensically acceptable determination of the amount of cocaine and benzoylecgonine present in the meconium sample. Generally, second aliquot portions of the pre-processed pooled meconium samples for these subject infants yielding a presumed positive by FPIA screen were spiked with trideuterated cocaine and benzoylecgonine as internal standards. The extraction procedure on the spiked pre-processed specimens included an initial extraction with acetic acid/acetone to provide a cocaine extract concentrate. The cocaine extract concentrate was buffered and centrifuged to separate neutral fats and lipids prior to further processing. The clarified extracts were buffered to a pH of 6.0 and subjected to a solid phase extraction employing a cationic solid phase extraction column to selectively isolate and separate cocaine and benzoylecgonine target analytes in a concentrated eluate. The eluate was treated to form trimethylsilyl derivatives of the spiked analyte analogs and sample analytes and the resulting derivatized solutions were analyzed by gas chromatography/mass spectrometry (GC/MS) on a Hewlett-Packard GC-MSD instrument.

Before performing the specialized extraction for cocaine and its metabolites, the following calibration standards and internal working controls and reagents were prepared:

Calibration Standards: 100 ng each of cocaine and benzoylecgonine spiked with 500 ng each of deuterated analogs were prepared. Cocaine-d3 and benzoylecgonine-d3 were used as the internal standards (0.1 ng/ml in methanol). Working internal standards included codeine, cocaine-d3 and benzoylecgonine-d3 at 20 micrograms per ml. 50 µl of working internal standard solution were added to all samples. In addition to the above standards and internal controls, the following reagent compositions were prepared. A 0.1M phosphate buffer, pH 6.0 was prepared by weighing out 13.61 g of a reagent grade potassium phosphate monobasic ($KH_2PO_4$) available from E-K INDUSTRIES and charging it into a 1.0 liter volumetric flask. The potassium phosphate monobasic was dissolved in 900 ml of de-ionized water. The pH was adjusted to 6.0 with 1.0M potassium hydroxide with stirring. The total volume was brought up to 1.0 liter with de-ionized water. The phosphate buffer reagent was stored at 5° C. and discarded every 30 days. A 1.0M potassium hydroxide solution was prepared by weighing 5.6 g of potassium hydroxide reagent grade into a 100 ml volumetric flask. The potassium hydroxide was dissolved with de-ionized water and brought to volume. The potassium hydroxide standard was stable at room temperature for three months. A 0.1M hydrochloric acid solution was prepared by adding 150 ml of de-ionized water to a 250 ml volumetric flask. 2.1 ml of concentrated hydrocholoric acid ACS reagent grade was added and the solution was further brought to volume with additional de-ionized water. The hydrochloric acid solution was stable at room temperature for three months. A methylene chloride:isopropyl alcohol (80:20) solvent solution with 2% ammonium hydroxide was prepared by adding 80 ml of methylene chloride and 20 ml of isopropanol to a 100 ml reagent bottle. The mix solvents were mixed and 2 ml were removed. Thereafter, 2 ml of ammonium hydroxide reagent grade were added to return the reagent volume to 100 ml. The 100 ml were transferred to a capped container and this reagent was prepared daily.

In accordance with this Example procedure, a specialized extraction for cocaine and benzoylecgonine metabolite was performed as follows:

A 1.0 g sample of pre-processed meconium previously testing positive in the FPIA screening procedure for cocaine was placed in a 16 by 125 disposable polypropylene tube. 50 µl of working internal standards containing 10 µg/ml of deuterated benzoylecgonine and deuterated cocaine each were added respectively. 3.0 ml of glacial acetic acid reagent grade were added to each sample. The acid and spiked sample were homogenized using an OMNI 5000 tissue homogenizer set at high speed for a period of at least 30 seconds until a substantially uniform homogenate was obtained. 6.0 ml of acetone and diphenylamine prepared in accordance with the method of Example 1 were added to each sample. The samples were vortexed and allowed to mix on a sample mixer for a period of about 5 minutes. Thereafter, the mixed two-phase samples were centrifuged at high speed for 5 minutes to resolve the two-phase mixture into a top organic phase and a lower second phase containing the meconium solids. The top organic phase was carefully transferred to a silanized 10 ml concentrator cup. The concentrator cup was placed in a sample concentrator set at 75° C. over air and vacuum. The volume of the organic phase in the concentrator cup was reduced to less than 0.5 ml, care being taken to make sure that the organic phase did not bump. Thereafter, 0.5 ml of absolute methanol was added to each concentrated sample and the sample was mixed thoroughly. The mixed sample was transferred to a clean 16 by 125 ml polypropylene tube and 6.0 ml of the 0.1M phosphate buffer pH 6 were added to each tube. The buffered concentrates were vortexed to mix thoroughly. Thereafter, the buffered concentrates were centrifuged at high speed for 5 minutes and any lipid layer at the top of the tube was carefully aspirated prior to proceeding. The outlet ends of an appropriate number of BOND ELUTE (CERTIFY) ONE brand extraction columns (VARIAN) were placed into the female end of the stock cock valves on the top of the vacuum manifold. An appropriate number of labelled polypropylene 16×125 mm tubes were employed as collection vessels and placed under each column in the vacuum manifold. The BOND ELUTE certified columns were conditioned by sequentially passing through each column a 2.0 ml of absolute methanol followed by 2.0 ml of the 0.1 M phosphate buffer pH 6. The column beds were not permitted to dry. The stock cock valves were closed as soon as the liquid phase reached the top of the frit.

Each buffered specimen was filtered through a 30 micron polypropylene frit as it was poured into the column reservoir. The vacuum was turned on and adjusted by the controller so that the flow rate through the column was about 2.0 ml per minute (5 to 10 inches of mercury). Thereafter, the column was sequentially rinsed by passing through the column 3.0 ml of de-ionized water, 3.0 ml of 0.1M hydrochloric acid solution and 9.0 ml of methanol. Receiving tubes were placed in the manifold rack and all needle tips were cleaned with lab tissue before replacing the manifold top. The rack was then placed within the manifold and the target analytes and analyte analogs were eluted by passing through each column 2.0 ml of the methylene chloride/ isopropanol (80/20, v/v) plus 2% $NH_4OH$ reagent solution prepared above. The eluate was transferred to 3.0 ml aluminum concentration vials and the extracts were dried on a hotplate over hot air with care being taken that the eluate phase does not bump. The residues were derivatized by adding 100 ml of 95% reagent grade ethanol to the dried residue. After swirling and mixing, the residue was transferred to auto-sampler vials containing 250 µl silanized inserts. The reconstituted residues were again taken to dryness in a vacuum oven set at 55° C. and 20 to 22 mm of mercury. The auto-sampler vials were capped securely and 40 µl of N-methyl-N-trimethylsilyltrifluorilacetamide (Pierce Chemicals) was added to each vial and the contents of each vial were vortexed. Thereafter, the vortexed mixture was heated for 15 minutes at 75° C. in a dry bath until derivatization was complete. 2.0 µl of the derivatized test solution was injected into the GC for analysis.

The parameters for the GC/MS operation were as follows: The column consisted of 5% phenyl-95% methylsilicone, 0.20 mm ID, 0.33 micron film thickness, 25M length. The GC conditions were set as follows: injector temperature—250° C.; transfer line temperature—270° C.; start temperature—100° C.; injection mode—splitless; purge time on—0.5 minutes. The instrument protocol was set as in the following program sequence: 100° hold 1 minute, ramp at 20° per minute until 300°, hold for 1 minute.

The GC/MS acquisition parameter file was setup to determine two groups of selected ions as follows:

|  | Quantitative Ion | Qualifiers |  |
| --- | --- | --- | --- |
| DRUG: Cocaine | 303 | 182 | 82 |

|  | Quantitative Ion | Qualifiers |  |
|---|---|---|---|
| DRUG: Benzoylecgonine | 361 | 240 | 82 |
| INTERNAL STANDARDS |  |  |  |
| $D_3$ - Cocaine | 306 | 185 |  |
| $D_3$ - Benzoylecgonine | 364 | 243 |  |

The samples were run through the GC/MS instrument and curves for the selected ions were generated.

The calculations used to determine quantitatively the amount of target analyte present in the meconium sample was based on comparing the native drug's response against the quantitatively known analogs. This technique allowed quantitative calculations based on a ratio of the native drug area versus the labelled analog area. This ratio is then multiplied by the amount of labelled analog in the extract in nanograms divided by the extracted amount in grams of sample. The internal standards were deuterated analogs of the compounds of interest and extraction recoveries and instrument responses are effectively equal. These two assumptions eliminate the requirement for recovery determinations since any factor affecting the response of the native drug will also affect equally the response of the deuterated analogs. The calculations may be represented by the following formula:

$$\text{Conc} = \frac{\text{Area of analyte} \times \text{Amount of analog (ng)} \times \text{Response}}{\text{(ng/g) Area of analog} \times \text{Extracted mass (g)} \times \text{factor}}$$

One criteria for the reporting of data was for the calculated ion ratio to be a certain percentage of expected ratios. These ratios were calculated using TARGET software on the Hewlett-Packard GC/MS data system. A relative 30% window was used for acceptable data so that an ion with an expected ratio of 60% would have a 42% to 78% window for an acceptable ion ratio range.

In accordance with this confirmatory procedure, the cocaine reporting range was determined to be from 5.0 ng/g to 10,000 ng/g for the meconium samples.

EXAMPLE 9

GC/MS CONFIRMATORY PROCEDURES FOR QUANTITATIVE DETERMINATION OF AMPHETAMINES IN MECONIUM SAMPLES

Generally, in accordance with this method meconium specimens previously testing positive by FPIA for amphetamines are extracted under alkaline conditions using liquid/liquid techniques. The samples are thereafter derivatized and analyzed by GC/MS using electron impact and selected ion monitoring mode.

Prior to extracting a second aliquot sample presumed positive by FPIA, the following reagent solutions and standards and controls were prepared. A 0.1% methanolic $H_2SO_4$ solution was prepared by mixing 100 ml of absolute methanol and 100 µl of concentrated sulfuric acid to form a stock reagent solution. The sulfuric acid solution was made fresh monthly. An extract salt/buffer mixture was prepared by mixing 6 parts of sodium chloride and 2 parts of sodium carbonate based on the weight of the overall salt/buffer mixture.

A special mixed organic extraction solvent was prepared by admixing volumetric amounts of heptane/methylene chloride/ethylene chloride/isopropanol in 50/17/17/16 ratios. A 2.40N aqueous hydrochloric acid solution was prepared by admixing 200 ml of concentrated hydrochloric acid with 800 ml of de-ionized water. A 0.10 N aqueous hydrochloric acid solution was prepared by mixing 991.7 ml of de-ionized water with 8.3 ml concentrated hydrochloric acid.

A 1.0 mg/ml d-amphetamine standard stock solution was prepared by adding 31.8 mg of d-amphetamine hydrochloride to a 25 ml volumetric flask and diluting to volume with absolute methanol. A 1.0 mg/mm methamphetamine standard stock solution was prepared by adding 31.0 mg of methamphetamine hydrochloride to a 25 ml volumetric flask and diluting to mark with absolute methanol.

A stock internal standard was obtained from RADIAN including a d-amphetamine-d5 solution containing 100 µg/ml12 and a methamphetamine-d8 standard solution containing 100 µg/ml. Working stock amphetamine/methamphetamine controls at 50 µg/ml concentration were prepared by adding 5.0 ml of the stock amphetamine and methamphetamine standards to a 100 ml volumetric flask and diluting to mark with absolute methanol. A working amphetamine methamphetamine control at 100 µg/ml concentration was prepared by adding 5.0 ml each of the stock amphetamine and methamphetamine controls to 100 ml volumetric flask and diluting to mark with absolute methanol. Finally, a working internal standard having a concentration of 10.0 µg/ml was prepared by transferring the contents of the stock d-amphetamine-d5 and methamphetamine-d8 solutions to a 10.0 ml volumetric flask and diluting to mark with absolute methanol. The negative control sample employed in the confirmatory assay comprised in-house drug-free meconium spiked with 100 ng/g methamphetamine and amphetamine.

In accordance with the amphetamine confirmatory procedure 0.5 to 1.0 g of presumptive positive meconium sample are placed in 16 by 125 ml polypropylene tubes. The samples are spiked with 10 µl of the working internal standards containing both d-amphetamine d5 and methamphetamine-d8. Thereafter, 5.0 ml of the 2.4N aqueous HCL solution was added to each sample. The acidified samples were homogenized using the OMNI 5000 tissue homogenator set at high speed for periods of at least 30 seconds until substantially uniform homogenates were prepared. The homogenate was centrifuged to define an aqueous acid top layer and a second pellet layer containing meconium solids. The top aqueous layer was transferred to clean 16 by 125 silanized glass screw-top tubes. Thereafter, the acidified samples were neutralized by adding 0.8 ml of a 12N sodium hydroxide solution followed by vortex mixing. After neutralizing, 2.0 g of the extraction/salt/buffer mixture were added to each tube. Thereafter, 5.0 ml of the mixed organic extraction solvent was added to each tube and the contents of each tube were mixed thoroughly for 5 minutes. Thereafter, the contents of the tube were centrifuged for 5 minutes and the top organic phase was transferred to clean 16 by 125 ml tubes. After being transferred to clean 16 by 125 tubes, the intermediate extract was again acidified by adding 2.0 ml of the 0.1N HCL solution to each tube. After mixing for 5 minutes, the solutions were centrifuged at high speed for 5 minutes and any top organic phase was aspirated and discarded. Thereafter, 2.0 g of the salt/buffer mix were added to each tube and 2.5 ml of the mixed organic extraction solvent were added and this mixture was again mixed for 5 minutes. Once again, this mixture was centrifuged at high speed for 5 minutes and the top organic phase was transferred to 3.0 ml aluminum vials. A drop of the 0.1% sulfuric acid in methanol was added to each tube to prevent entraining of analyte. Thereafter, the organic samples were taken to dryness on a hotplate with forced air. The samples were reconstituted with a 100 µl of ethyl alcohol reagent grade with swirling to aid dilution. The alcohol solution was transferred to auto-sampler vials and again taken to dryness in a vacuum oven set at 55° C. with a vacuum of 20 to 22 mm of mercury. 30.0 µl of isooctane and 10.0 µl of an N-methylbis(heptafluorobutyramide) derivatizing agent were added. The sealed vials were then placed in heating blocks at 75° C. for 30 minutes to permit derivatization to proceed until substantially complete. The derivatized samples were cooled to room temperature prior to injecting into the GC/MS for determination in accordance with the method of Example 8. For this amphetamines confirmatory procedure the GC conditions were set as follows: Injector temperature—225° C.; transfer line temperature—250° C.; start temperature—100° C., hold for 1 minute; the injection mode—splitless; and purge time on was 0.5 minutes The program protocol was set at 100° hold 1 minute, ramp at 20°/minute to 260° and hold for 1 minute. The mass monitored ions were selected as follows:

|                  |     |     |     |
|------------------|-----|-----|-----|
| Amphetamine      | 240 | 118 | 91  |
| Methamphetamine  | 254 | 210 | 118 |
| Amphetamine-D5   | 244 | 123 |     |
| Methamphetamine-D8 | 261 | 213 |   |

The concentration of amphetamine and methamphetamine target analytes present in the meconium samples was determined in ng/g by calculating the ratio of the response area of the amphetamine or methamphetamine native drug area versus the area of the labelled deuterated analogs times the amount of the labelled drug divided by the extracted mass as set forth in accordance with the formula in Example 8.

In accordance with the new and improved confirmatory procedure the cut-off limit for detecting amphetamine or methamphetamine target analytes in a meconium sample is 50 ng/g. It has been determined that the limits of linearity for the GC/MS confirmatory assay procedure extends from 50 to 5,000 ng/g. Values over 5,000 ng/g are simply reported as >5,000 ng/g. Values less than 50 ng/g are reported as a negative finding for amphetamine or methamphetamine analyte.

EXAMPLE 10

GC/MS CONFIRMATORY PROCEDURE FOR QUANTITATIVE DETERMINATION OF OPIATE ANALYTES IN MECONIUM SAMPLES

In accordance with this general procedure, meconium specimens previously testing to be as presumptive positive by FPIA in accordance with the method of Example 4 are extracted under alkaline conditions using liquid/liquid extraction techniques. The samples are derivatized and then analyzed by GC/MS using electron impact and selected ion monitoring mode. The GC/MS procedural protocols generally followed the procedures outlined in Examples 8 and 9 identified above. The standard reagent solutions and calibration standards prepared for this assay were as follows: An extraction salt buffer mixture was prepared by mixing 6 parts of sodium chloride, 1 part of sodium bicarbonate and 1 part of sodium carbonate based on the total weight of the salt/buffer mixture. A 2.4N aqueous HCL solution was prepared by mixing 207 ml of concentrated reagent grade HCL with 793 ml of deionized water.

Calibration standards and internal controls were prepared by taking 100 ng each of morphine and codeine spiked with 500 ng each of deuterated analogs. The standards are derivatized identically to authentic meconium extracts and analyzed. The peak area ratio is placed into the target calibration files. The deuterated analyte analogs used as internal standards selected were morphine-$D_3$ and codeine-$D_3$ in concentrations of 0.1 mg/ml in methanol. Working internal standards for morphine-$D_3$ and codeine-$D_3$ were prepared to contain 10 µg/ml of the internal standards. 50.0 µl of the internal standards were added to all tubes. The deuterated morphine and codeine reagents were supplied by RADIAN CORPORATION, Austin, Tex. Negative internal controls were prepared from in-house drug-free meconium spiked at 100 ng/g with 100 µl of the low meconium spiking control samples.

In accordance with the new and improved opiate assay confirmatory assay, an extraction was performed by placing 0.5 to 1.0 g of pre-processed meconium in a 16 by 125 polypropylene tube. 50.0 µl of working internal standards containing both codeine-$D_3$ and morphine-$D_3$ were added to each tube. Thereafter, 5.0 ml of 2.4N aqueous hydrochloric acid solution were added to each tube and specimen. The contents of each tube were homogenized using the OMNI 5000 tissue homogenator for a period of at least about 30 seconds to achieve a smooth, uniform homogenate. The acidified homogenized samples were then centrifuged at high speed for 5 minutes. The top aqueous layer was transferred to a new 16×125 silanized glass screw-top tube and 5 ml of methytertbutylether were added and mixed for a period of about 5 minutes. The two-phase mixture was permitted to separate and the top organic layer was carefully aspirated and discarded. The aqueous acid layer was then neutralized with 0.8 ml of 12N sodium hydroxide and vortexed. Thereafter, 7.5 ml of methyl-t-butyl ether were added to each tube and 2.0 g of the salt/buffer mixture were added to each tube. The neutralized buffered mixtures were mixed for 5 minutes, centrifuged at high speed for 5 minutes and the top organic phase was transferred to 10.0 ml glass concentration vials. The contents of the glass concentration vials were evaporated to dryness in an Alltech sample evaporator under air and vacuum. Target analyte and analog values were reconstituted in 100 µl of ethanol with swirling to aid dilution. The ethanolic solutions were transferred to auto-sampler vials and again evaporated to dryness in a vacuum of and set at 75° C. and a vacuum of 20 to 22 mm of mercury. After being tightly capped, 40.0 µl of N-methyl-N-trimethylsilyltrifluoroacetamide derivatizing agent from Pierce Chemicals was added. The vials were placed in heating block at 75° C. for 10 minutes to permit the derivatization reaction to proceed to completion. The derivatized samples were then permitted to cool to room temperature before injecting in the GC/MS instrument.

The GC/MS injection procedure was substantially in accordance with the method outlined in Examples 8 and 9. The GC conditions were set so that the injector temperature was 250° C. the transfer line temperature was 270° C. the start temperature 100° C. hold for 1 minute, the injection mode was splitless and the purged time on was 0 5 minutes. The first program was set to heat to 100°, hold for 1 minute, ramp at 20° per minute to 300° and hold for 1 minute. The following ion peak qualifying parameters were employed:

| DRUG | ION | DWELL TIME |
|---|---|---|
| GROUP 1 | | |
| Codeine-$D_3$ | 346 | 50 |
| Codeine-$D_3$ | 374 | 50 |
| Codeine | 343 | 50 |
| Codeine | 234 | 50 |
| Codeine | 371 | 50 |
| GROUP 2 | | |
| Morphine-$D_3$ | 417 | 50 |
| Morphine-$D_3$ | 432 | 50 |
| Morphine | 401 | 50 |
| Morphine | 414 | 50 |
| Morphine | 429 | 50 |

The ion parameters are set to give the internal standard quantification ion area count greater than 50,000 and allow for reproducible acquisition of 3 ions for the native drug and 2 ions for its deuterated analog. The concentration of opiates present was calculated by comparing the ratio of the response area for the native drug versus the response area of the labelled analog multiplied by the amount of labelled drug in nanograms divided by the extracted mass in grams. Once again because of the use of internal standards and controls the response factor is 1.

The GC/MS confirmatory procedure for opiates has a lower cut-off detection concentration limit of 25 ng/g. The limits of linearity for the procedure are from 25 ng to 1,000 ng/g. Values greater than 1,000 ng/g are reported as >1,000 ng/g and values less than 25 ng/g are reported as negative for opiate analytes.

EXAMPLE 11

GC/MS CONFIRMATION PROCEDURE FOR QUANTITATIVELY DETERMINING TETRAHYDRO-CANNABINOL ANALYTE IN MECONIUM SAMPLES

A GC/MS extraction technique and determination was performed on meconium samples previously testing positive by the preliminary FPIA screening method of Example 5. Generally, in accordance with this GC/MS confirmatory procedure a presumptive positive sample of meconium is spiked with deuterated THC-COOH analog followed by homogenization, alkaline hydrolysis, acidification, liquid/liquid extraction followed by derivatization. More particularly, the following reagent solutions, calibrators and controls were prepared prior to extraction.

The calibration standards employed in the assay were for 100 ng of 11-nor-Delta-9-tetrahydrocannabinol-9-carboxylic acid spiked with 100 ng of a deuterated analog. The deuterated analog, THC-COOH-$D_3$ is used as the internal standard as a solution of 0.1 mg/ml in methanol. The working internal standard for THC-COOH-$D_3$ was 2.0 μg/ml and 50 μl were added to all tubes.

An organic extraction solvent mixture of N-hexane/ethyl acetate (90/10,v/v) was prepared by adding 100 ml of ethyl acetate to 900 ml of N-hexane in a reagent bottle. An 11.8N potassium hydroxide solution was prepared by dissolving 66.2 g of potassium hydroxide in 75 ml of de-ionized water in a 150 ml beaker. Once dissolved the solution was poured into a 100 ml volumetric flask and filled with de-ionized water to the volume mark.

An in-house 100 ng calibrator or equivalent was analyzed with each run and calibration was performed on the H-P data system using TARGET software. In addition, in-house pooled meconium positive samples for cannabinoid known to contain 58 ng/g of THC-COOH are added in a blank drug-free meconium sample are also run with each batch as quality controls.

In accordance with this new and improved confirmatory method for quantifying THC metabolite, a 0.5 to 1.0 g sample of pre-processed meconium testing as presumptively positive by FPIA was placed in 16 by 125 mm polypropylene sample tubes. 50 μl of a working internal standard are added, 3.0 ml of methanol are added and the samples are homogenized using an OMNI 5000 tissue homogenizer set at high speed for a period of about at least 30 seconds until a homogenate is formed. The homogenized sample is permitted to stand for at least 5 minutes. Thereafter, 0.5 ml of an 11.8N potassium hydroxide solution is added to each tube and the contents are vortexed. After thorough mixing, the contents are centrifuged at high speed for 5 minutes and the top organic phase is transferred to a clean 16 by 125 silanized glass tube. 3.0 ml of de-ionized water and 6.0 ml of the mixed ethyl acetate/N-hexane extraction solvent are added to each tube. The contents are vortexed and then permitted to incubate on a sample mixer for a period of about 15 minutes. The top organic phase is aspirated and discarded and 0.8 ml of concentrated hydrochloric acid are added to each tube and the contents are vortexed. 8.0 ml of the mixed extraction solvent are added to the tube and the sample is again mixed for a period of about 5 minutes. After centrifuging at high speed for 5 minutes, the top organic phase is transferred to silanized concentration cups and placed in a sample concentrator set at 75° C. and dried over air and vacuum. The dried residues are reconstituted with 100 μl of ethanol and the ethanol solution is transferred to an auto-sampler vial containing 250 μl silanized liners. Again the sample is taken to dryness in a vacuum oven set at 70° to 85° C. at a vacuum of 20 to 25 inches of mercury without permitting the solvents to bump. Derivatization was accomplished by capping and crimping each auto-sampler vial and thereafter adding 25 μl of N-methyl-N-trimethylsilyltrifluoroacetamide derivatizing agent to each vial. The contents of each vial are permitted to react and derivatize for a period of about at least 15 minutes at 75° C. Thereafter, the derivatized sample is permitted to cool prior to being injected into the GC/MS instrument. 2.0 μl of the derivatized sample are injected into the GC/MS system. The selected ions monitored for THC were non-deuterated 371.30, 473.30, 488.30 and for the deuterated THC ions at 374.30 and 491.30.

The samples and calibrators were run through the GC/MS instrument and the concentration of THC carboxylic acids were determined by determining the ratio of the native drug area versus the labelled analog area and thereafter multiplying that ratio by the amount of labelled analyte present in the extract divided by extract mass to yield the concentration of marijuana metabolite present in the meconium sample in ng/g of sample tested. The reporting range for this confirmatory assay has been determined to be from about 10 to 200 ng/g. Samples quantifying at less than 10.0 ng/g are reported as negative. Those quantifying as greater than 200 ng/g are reported as greater than 200 ng/g. For the above procedures the GC conditions were set at 250° C. injector temperature, the transfer line temperature was 270° C. the starting temperature was 100° C., holding for 1 minute, the injection mode was set at splitless and the purge time on was 0.5 minutes The program used was 100° hold 1 minute, ramp at 20° per minute to 320°.

EXAMPLE 12

GC/MS CONFIRMATORY PROCEDURE FOR QUANTITATIVE DETERMINATION OF PHENCYCLIDINE ANALYTE IN MECONIUM SAMPLES

In accordance with this Example, a quantitative determination of phencyclidine concentration is made by performing a solid phase extraction of homogenized and protein denatured meconium sample previously testing as presumptively positive by FPIA assay for phencyclidine. The phencyclidine concentration is confirmed and the level determined by monitoring its major ions and comparing them with spiked internal standards. Prior to an extraction procedure the following calibration standards, reagents and internal controls were prepared. As calibration standards, 25 ng of phencyclidine spiked with 50 ng of the deuterated analog PCP-$D_5$ were prepared. Phencyclidine-$D_5$ is used as the internal standard at 0.1 mg/ml in HPLC grade methanol. The working internal standard for PCP-$D_5$ is 10.0 µg/ml and 25 µl were added to all tubes. The phencyclidine-$D_9$ deuterated drug analog is supplied by RADIAN CORPORATION, Austin, Tex. The following reagents were prepared: A 0.1M phosphate buffer having a pH of 6.0 was prepared by adding 13.61 g of potassium phosphate monobasic into a 1.0 liter volumetric flask. 900 ml of de-ionized water were added to dissolve the potassium phosphate monobasic and the pH was adjusted to 6.0 with 1 M potassium hydroxide while stirring. Thereafter, the total volume was diluted to mark with de-ionized water. The solution was stored at 5° C. and discarded every 30 days. A 1M potassium hydroxide solution was prepared by weighing 5.6 g of potassium hydroxide and adding it to a clean 100 ml volumetric flask. The potassium hydroxide was dissolved with de-ionized water and diluted with deionized water to the volume mark. This reagent solution was stable at room temperature for three months. A 1.0M acetic acid solution was prepared by adding 15 ml of deionized water to a 100 ml volumetric flask. 5.75 ml of glacial acetic acid were added to the flask and the flask was diluted to volume with additional deionized water. This reagent solution was stable at room temperature for 2 months. An ethyl acetate with 2% ammonium hydroxide reagent solution was prepared by adding 98 ml of ethyl acetate to 100 ml reagent bottle and thereafter adding 2.0 ml of ammonium hydroxide. The ethyl acetate 2% ammonium hydroxide solution was prepared fresh daily. A 1.67 mg/liter diphenylamine in acetone reagent solution was prepared by adding 6.67 mg of diphenylamine into a new 4 liter bottle of reagent grade acetone. The contents were shaken to mix thoroughly and were stable at room temperature for 12 months. Finally a 0.1% sulfuric acid in methanol solution was prepared by adding 100 µl of concentrated sulfuric acid to 100 ml of methanol and storing the solution in a capped container.

Controls for the assay were prepared by taking known in-house drug-free meconium samples and spiking them at a loading level of 50 ng/g. Also a negative drug-free meconium sample was run as a calibrated control.

In accordance with the new and improved confirmatory extraction method a 0.5 to 1.0 g sample of meconium previously tested presumptively positive for PCP content was placed in a 16 by 125 polypropylene tube. 25 µl of the deuterated PCP analog PCP-$D_5$ are added to each specimen tube. 3.0 ml of glacial acetic acid are added to each specimen and the acidified tissue sample was homogenized using a tissue homogenizer set at high speed for at least about 30 seconds. Thereafter, 6.0 ml of the acetone/diphenylamine reagent is added to each tube. The contents of the tubes are vortexed and then allowed to mix for 5 minutes. The organic phase is separated from a second phase containing meconium solids by centrifugation at high speed for a period of at least about 5 minutes. The top organic phase was transferred to a 10 ml concentration cup. A drop of 0.1% $H_2SO_4$ in MeOH was added to each tube to prevent inadvertent loss of analyte. Thereafter, the concentration cups were placed in a sample concentrator at 75° C. over air and vacuum and the volume of each sample was reduced to less than about 0.5 ml, care being taken that the samples do not bump during drying. Thereafter, 0.5 ml of methanol were added to each cup and the samples were mixed thoroughly and transferred to clean 16 by 125 polypropylene tubes. 6.0 ml of 0.1M phosphate buffered pH 6.0 were added to each tube and the solutions were vortexed thoroughly. Thereafter, the solutions were centrifuged at high speed for 5 minutes and any lipid top layer is very carefully aspirated and discarded before proceeding. An appropriate number of BOND ELUTE (CERTIFY) ONE solid phase extraction columns are attached to the female ends of stock cock valves mounted on the top of the vacuum manifold. An appropriate number of labelled polypropylene tubes as collection vessels were placed under each column in the vacuum manifold. Each of the columns was conditioned by sequentially passing through each column 2.0 ml of methanol and 2.0 ml of the 0.1M phosphate buffer having a pH of 6.0. The columns were not permitted to go to dryness. Each of the prepared buffered specimens were passed into column reservoirs and the vacuum was adjusted so that the flow rate through the column was set at about 2.0 ml/minute (5–10 inches of mercury). After the sample was passed through the column, the column was rinsed sequentially by passing through 1.0 ml of a 1.0M acetic acid solution and dried under full vacuum for 5 minutes. Thereafter, 6.0 ml of methanol are flowed through the column and the column is dried under full vacuum for 2 minutes. Receiving tubes were placed in the manifold rack and needle tips were wiped with lab tissue and the manifold top was replaced. Phencyclidine target analytes and analyte analogs were eluted from the column by passing through each column 2.0 ml of the ethyl acetate containing 2% ammonium hydroxide solution. The eluate is transferred to a 3.0 ml aluminum concentration vial and 1 drop of 0.1% sulfuric acid and methanol is added to each tube. The extracts were then dried on a hotplate over hot air making sure the extracts do not bump. The dried residues were reconstituted with 50 µl of a mixed isooctane/isopropanol 80/20 V/V mixed solvent. The reconstituted residue is transferred to auto-sampler vials containing silanized 250 µl limited volume inserts. The caps are placed and crimped on each vial and the samples are injected into GC/MS.

The gas chromatograph settings were set at initial temperature of 80° C., the transfer line temperature was set at 250° C., the start temperature was set at 80° C. hold for 1 minute Injection mode was splitless, the purge time on was 0.5 minutes. The program was set to run at 80° hold for 1 minute, ramp at 22.5° C./minute to 250° C.

The ions monitored were for phencyclidine, quantitative ion—200 and qualifiers at 243/200 and 242/200. The phencyclidine internal standard control quantitative ion was 205 and single qualifier at 248/205 was used. The samples and negative controls and calibrators were run through the GC/MS instrument and the amount of PCP present in the meconium sample was quantitatively determined. The PCP reporting range for this assay has been determined to be from 25 ng to about 200 ng/g of meconium. Samples quantifying at as having less than 25 ng/g are reported as negative. Those samples quantifying at greater than 200 ng/g are simply reported as greater than 200 ng/g.

EXAMPLE 13

ALTERNATE METHOD FOR MAKING CONCENTRATED COCKTAIL MECONIUM EXTRACT FOR PRELIMINARY SCREENING BY FLUORESCENCE POLARIZATION IMMUNOASSAY METHODS

An alternate new and improved extraction procedure for liberating substantially all of the target analytes from the meconium matrix to form a concentrated meconium "cocktail" extract follows:

A number of reagent solutions were prepared prior to performing the extraction. A 0.1M phosphate buffer, pH 3.0, was prepared by weighing 13.61 grams of reagent grade potassium phosphate, monobasic, ($KH_2PO_4$, MW136.09) and adding it to a one liter volumetric flask. The potassium phosphate was dissolved into 900ml of de-ionized water. The pH of the solution was adjusted to 3.0 with phosphoric acid, while stirring. The adjusted solution was brought to a total volume of 1.0 liters by further addition of de-ionized water. The phosphate buffer solution was appropriately labeled.

A 0.1M hydrochloric acid solution was prepared by adding 150ml of de-ionized water into a 250ml volumetric flask. ACS reagent grade concentrated hydrochloric acid in the amount of 2.1 ml is then added. The solution was brought to volume (250 ml) by the further addition of de-ionized water. The hydrochloric acid solution was labeled and should be stable at room temperature for approximately three months.

A solution of methylene chloride and isopropyl alcohol (80:20) with 2% ammonium hydroxide was prepared by adding 80 ml of reagent grade methylene chloride and 20 ml of reagent grade isopropyl alcohol into a 100 ml reagent bottle. The solution was mixed and thereafter 2 ml of the solution was removed. Then 2 ml of ammonium hydroxide was added and the solution was transferred to a capped container. The solution should be prepared fresh daily and appropriately labeled.

A solution of acetonitrile and water (40:60) was prepared by adding 400 ml of acetonitrile into a 1000 ml graduated cylinder. The solution was adjusted to the volume of 1000 ml by addition of de-ionized water. This solution is mixed well and stored in an appropriately labeled glass vessel. The solution should be stable for approximately one year.

A methanol and triphenylamine solution (1 mg amine per liter alcohol) was prepared by adding 4 ml of 1 mg/ml triphenylamine into a 4 liter bottle of HPLC grade methanol. The solution was appropriately labeled and stored in glass at room temperature. The solution should be stable for approximately one year.

A stable buffer comprising a 50/50 volume/volume mixture of Abbott $AD_x$ buffer in absolute methanol was prepared by mixing equal portions of the $AD_x$ buffer and HPLC grade methanol together in a suitable sized container. The $AD_x$ buffer/methanol reagent solution was labeled appropriately.

A 0.1 percent $H_2SO_4$ in MeOH solution was prepared by pipetting 100 microliters of concentrated sulphuric acid (98%) into 100ml of HPLC grade methanol. The alcoholic sulphuric acid solution was labeled appropriately and should be storage stable for approximately one month.

After preparation of the reagents the alternate new and improved cocktail extract method is performed in accordance with this invention as follows:

A 1.0 gram sample of the pre-process neonatal meconium obtained in Preparation B set forth above is placed in a 16×125mm polypropylene tube for performing the extraction procedure set forth below.

Negative control samples are prepared by weighing 1.0 gram samples of drug-free meconium and performing the extraction procedure as set below to provide the negative control fluid extract for use in the FPIA assay. The control fluid is labeled Negative Control and dated with the date of preparation and an expiration date of one calendar year.

Positive meconium controls are prepared for extraction in accordance with the procedure set forth below by first spiking 1.0 gram samples of drug-free meconium with a 100 mcl aliquot of a meconium control spiking solution made-up to contain the following:

| | |
|---|---|
| Amphetamine | 1000 ng/ml |
| Methamphetamine | 1000 ng/ml |
| PCP | 500 ng/ml |
| THC-COOC | 500 ng/ml |
| Morphine | 1000 ng/ml |
| Codeine | 1000 ng/ml |
| Benzoylecgonine | 1000 ng/ml |
| Cocaine | 1000 ng/ml |
| Cocaethylene | 1000 ng/ml |
| Methadone | 1000 ng/ml |

The control fluid is labeled as Positive Control and dated with the date of preparation and an expiration date of one calendar year.

The extraction process starts with 3.0 ml of the methanol/triphenylamine reagent being added to the polypropylene tube and sample. The methanol/triphenylamine and pre-processed meconium are homogenized, for example by using an Omni 5000 tissue homogenizer set at the highest speed for a period of at least 15 seconds, until a smooth, substantially uniform finely-divided homogenate was formed. These steps denature the protein matrix and release the drug bound to protein into the methanol phase. The homogenate is vortexed and then centrifuged at high speed for 5 minutes. After centrifugation, a two-phase mixture is present including an organic top phase and a lower second phase including the meconium solids. The top organic methanol phase is decanted to a clean 16×125 mm polypropylene tube. 12 ml of 0.1M phosphate buffer, pH 3.0, are added to each tube.

Each of the buffered specimens is eluted through a mixed mode cationic exchange and $C_8$ reversed phase conditioned column under vacuum as follows: The outlet end of an appropriate number of extraction columns such as 15 ml Clean Screen Extraction Columns (Worldwide Monitoring) are placed into the female end of the stopcock valve on the top of a vacuum manifold equipped with a manifold rack. An appropriate number of labeled polypropylene 16×125mm tubes are placed under each column in the vacuum manifold as collection vessels. The columns are conditioned by sequentially passing through each column, 3 ml of methanol, another 3 ml of methanol, 3 ml of de-ionized water, and 3 ml of 0.1M phosphate buffer pH 3.0. The respective vacuum manifold stopcock valve is closed as soon as the phase reaches the top of the frit and the column bed is not allowed to dry. The target analytes are now extracted via a reverse phase mechanism. Each buffered specimen is poured through a filter (preferably a polypropylene filter is used) into the column reservoir. The vacuum is started and the controller is adjusted so that flow is about 2 ml per minute (5–10 in./Hg). The column is allowed to dry. The column is then rinsed and made acidic to enhance cation exchange by passing through the column sequentially 3 ml of de-ionized water and 1 ml of 0.1M hydrochloric acid. The column is again allowed to dry. The vacuum is turned off and the receiving tubes are placed in the manifold rack. Care is taken to wipe the needle tips with a lab tissue before replacing the manifold top. The vacuum manifold is set to collect. Each column is rinsed with 3 ml of methanol to elute acidic and neutral target analytes (basic analytes are retained via the cationic exchange mechanism) and the rinse eluate is collected for THC analysis. The columns are allowed to dry under vacuum for 5 minutes. The rinse eluate is removed and saved in clean receiving tubes. The basic analytes such as cocaine, PCP, opiates, methadone, and amphetamines are eluted with a stronger base by passing 3 ml of the methylene chloride: isopropanol (80:20)–2 percent ammonium hydroxide solution through each column. The eluate is transferred to 3 ml aluminum concentration cups and allowed to dry over air without hot plate heat. After approximately 3 minutes, one drop of 0.1 percent $H_2SO_4$ is added.

12.0 ml of the acetate buffer solution (pH 4.0) is added to each tube containing the acid/neutral methanoic extracted fraction saved from the first column extraction.

The samples are further eluted through a mixed mode anionic exchange and $C_8$ reversed phase conditioned column under vacuum as follows: the appropriate number of 15 ml Speed Scan THC Extraction Columns (Applied Separations) are connected to the valves on top of the vacuum manifold. The columns are conditioned by sequentially passing through each column 2 ml of methanol and 2 ml of de-ionized water. The column bed is not allowed to dry, and each buffered specimen is poured into the column reservoir to extract the acidic and neutral analytes via a reversed phase mechanism. The vacuum is started and adjusted so that flow is about 2 ml per minute (10–15in./Hg). The column is again allowed to dry. The column is rinsed with 2 ml of the acetonitrile/water (40:60) solution and then the column is allowed to dry. The vacuum manifold is positioned to collect and the acidic analytes in the samples are eluted by simple reversed phase elution with 3 ml of methanol under low vacuum.

The eluate is transferred into the appropriately labeled aluminum concentration cup used in the first extraction. The samples are dried over air with low hot plate heat. The samples are removed from the heat immediately when dry. The samples are reconstituted with 250mcl of the $AD_x$/methanol (50/50) solution. The respective liquid phases of the samples are transferred, as necessary, to appropriate sample vessels for analysis. For example, the samples can be analyzed for cocaine metabolites, phencyclidine, opiates, methadone, amphetamines, and cannabinoids using FPIA utilizing the same general procedure set forth in the foregoing Examples 2–6, respectively.

This particular method is particularly useful to provide a concentrated extract containing a wide range of both basic and acidic-neutral analytes which can be screened and/or analyzed by variety of methods. For instance, cocaine metabolites, opiates, cannibinoids, amphetamines, phencyclidine, methadone, barbituates, benzodiazepines, methaqualone, and propoxyphene to name but a few analytes can be tested by enzyme multiplied immunoassay, fluorescence polarization immunoassay and gas chromatography/mass spectrometry.

EXAMPLE 14

COMPARATIVE EXTRACTION EFFICIENCIES OF MECONIUM TISSUE SAMPLE BY THE METHODS OF EXAMPLE 1 AND EXAMPLE 13

Concern has been expressed that simple meconium extracts for drugs of abuse, including the method of Example 1, have a sufficient lipid content in the final extract to show a significant negative bias. The following comparative data demonstrate that the method of Example 13 sufficiently reduces the lipid content of the final extract to significantly reduce any negative bias associated with such lipid content.

The alternate new improved meconium extraction procedure of Example 13 was compared with the extraction method of Example 1 for the analytes Cannabinoids (THC), Cocaine metabolites (COC), Opiates (OP), Phencyclidine (PCP), Amphetamines (AMP), and Methadone (MDON). 50 positive control specimens and 50 negative control specimens were analyzed using the extraction method of Example 13 and the extraction method of Example 1. Fluorescence polarization immunoassay was used as the detection method to eliminate any immunoassay bias. Positive control specimens contained 50 nanograms per gram (ng/g) of Carboxy-THC and PCP and 100 ng/g of Benzolylecgonine, Morphine, Codeine, Amphetamine, Methamphetamine, and Methadone. The following results were obtained:

|  | Example 1 | Example 13 |
|---|---|---|
| POSITIVE CONTROL | | |
| THC Mean | 6.71 ng/ml | 126.7 ng/ml |
| SD | 28.74 | 21.47 |
| COC Mean | 72.2 ng/ml | 271.9 ng/ml |
| SD | 44.7 | 103.1 |
| OP Mean | 252.1 ng/ml | 248.0 ng/ml |
| SD | 110.5 | 75.4 |
| PCP Mean | 32.9 ng/ml | 94.37 ng/ml |
| SD | 14.50 | 11.47 |
| AMP Mean | 1511 ng/ml | 1987 ng/ml |
| SD | 781 | 57.9 |
| MDON Mean | 32.9 ng/ml | 72.74 ng/ml |
| SD | 12.99 | 17.79 |
| NEGATIVE CONTROL | | |
| THC Mean | 3.88 ng/ml | 8.46 ng/ml |
| SD | 19.39 | 9.70 |
| COC Mean | 25.8 ng/ml | 9.02 ng/ml |
| SD | 44.6 | 19.17 |
| OP Mean | 28.56 ng/ml | 1.97 ng/ml |
| SD | 25.51 | 4.87 |
| PCP Mean | 1.40 ng/ml | 5.09 ng/ml |
| SD | 1.98 | 3.38 |
| AMP Mean | 1251 ng/ml | 193.2 ng/ml |
| SD | 907 | 415.5 |
| MDON Mean | 3.97 ng/ml | 1.32 ng/ml |
| SD | 4.86 | 1.25 |

Using an instrument cutoff value of 20 ng/ml of analyzed fluid for THC, 25 ng/ml for PCP, OP, and MDON, 50 ng/ml for COC, and 1000 ng/ml for AMP, the following results were obtained:

|  | Example 1 | Example 13 |
|---|---|---|
| THC POS | 2/50 | 50/50 |
| 50 ng | 4% | 100% |
| THC NEG | 48/50 | 48/50 |
| 0 ng/g | 96% | 96% |
| COC POS | 27/50 | 50/50 |

|  | Example 1 | Example 13 |
| --- | --- | --- |
| 100 ng/g | 54% | 100% |
| COC NEG | 43/50 | 46/50 |
| 0 ng/g | 86% | 92% |
| OP POS | 50/50 | 50/50 |
| 200 ng/g | 100% | 100% |
| OP NEG | 24/50 | 50/50 |
| 0 ng/g | 48% | 100% |
| PCP POS | 28/50 | 50/50 |
| 50 ng/g | 56% | 100% |
| PCP NEG | 50/50 | 50/50 |
| 0 ng/g | 100% | 100% |
| AMP POS | 35/50 | 50/50 |
| 200 ng/g | 70% | 100% |
| AMP NEG | 20/50 | 47/50 |
| 0 ng/g | 40% | 94% |
| MDON POS | 27/50 | 50/50 |
| 100 ng/g | 54% | 100% |
| MDON NEG | 50/50 | 50/50 |
| 0 ng/g | 100% | 100% |

The method of Example 13 had 100% sensitivity at these detection levels and had over 90% specificity for true negatives.

EXAMPLE 15

COMPARATIVE EXTRACTION EFFICIENCES OF MECONIUM TISSUE BY THE METHODS OF EXAMPLE 13 AND METHODS DISCLOSED IN U.S. PAT. NO. 5,015,289 AND 5,185,267

The meconium extraction procedure of Example 13 was further compared with the method disclosed in U.S. Pat. No. 5,015,289 (Ostrea I) of contacting a sample of meconium with water and concentrated HCl, agitating the mixture then filtering the mixture through a glass wool filter, centrifuging the filtrate and testing the supernatant fluid. The method of Example 13 was also compared to the method disclosed in U.S. Pat. No. 5,185,267 (Ostrea II) of adding an aqueous phosphate buffer and methanol solution (<30% methanol) to a sample of meconium. The sample is agitated, then centrifuged. The supernatant fluid is transferred to a microcentrifuge vessel and centrifuged again, and a portion of the supernatant fluid is assayed. 50 positive control specimens and 50 negative control specimens were analyzed for the analytes Phencyclidine (PCP) and Methadone (MDON) using the method of Example 13 and the two Ostrea methods. Fluorescence polarization immunoassay was used as the detection method to eliminate any immunoassay bias. Positive control specimens contained 50 nanograms per gram (ng/g) of PCP and 100 ng/g of methadone. The following results were obtained:

|  | Ostrea I | Ostrea II | Example 13 |
| --- | --- | --- | --- |
| POSITIVE CONTROL | | | |
| PCP Mean | 2.08 ng/ml | 3.44 ng/ml | 94.37 ng/ml |
| SD | 1.26 | 2.38 | 11.47 |
| MDON Mean | 1.13 ng/ml | 0.83 ng/ml | 72.74 ng/ml |
| SD | 1.78 | 0.95 | 17.79 |
| NEGATIVE CONTROL | | | |
| PCP Mean | 2.09 ng/ml | 1.90 ng/ml | 5.09 ng/ml |
| SD | 1.16 | 2.34 | 3.38 |
| MDON Mean | 1.10 ng/ml | 0.32 ng/ml | 1.32 ng/ml |
| SD | 1.45 | 0.61 | 1.25 |

Using an instrument cutoff value of 25 ng/ml of analyzed fluid for both PCP and MDON, the following results were obtained:

|  | Ostrea I | Ostrea II | Example 13 |
| --- | --- | --- | --- |
| PCP POS | 0/50 | 0/50 | 50/50 |
| 50 ng/ml | 0% | 0% | 100% |
| PCP NEG | 50/50 | 50/50 | 50/50 |
| 0 ng/ml | 100% | 100% | 100% |
| MDON POS | 0/50 | 0/50 | 50/50 |
| 100 ng/ml | 0% | 0% | 100% |
| MDON NEG | 50/50 | 50/50 | 50/50 |
| 0 ng/ml | 100% | 100% | 100% |

Neither of the Ostrea methods was capable of detecting the presence of PCP or methadone at the 50 ng/ml and 100 ng/ml levels respectively, yielding sensitivity of 0%. The method of Example 13 had 100% sensitivity at these detection levels and had 100% specificity for true negatives.

I claim:

1. A method for preparing a concentrated neonatal meconium extract containing both basic and acidic-neutral target analytes present, if any, in a sample of infant meconium suspected of containing said target analytes, said method comprising:

providing a test sample of newborn meconium suspected of containing said target analytes;

adding substantially non-aqueous methanol solution to said sample to form a first mixture;

agitating said first mixture for a time sufficient to release substantially all of said target analytes from the meconium sample, until a substantially uniform homogenate is obtained, said homogenate including a liquid organic component;

separating said liquid organic component from said homogenate; and, separating said target analytes from said organic component by sequential extraction through mixed mode extraction columns, at least one of said columns comprising a cationic exchange resin and at least one of said columns comprising an anionic exchange resin.

2. The method of claim 1 wherein said first separating step is performed by centrifuging the homogenate to form a two-phase mixture including an organic phase comprising said organic component and a second phase.

3. The method of claim 1 further including the step of buffering said organic component prior to said column separation step.

4. The method of claim 3 wherein said buffering comprises addition of a phosphate buffer with a pH of approximately 3 to said organic component.

5. The method of claim 1 wherein said substantially non-aqueous methanol includes an amine component.

6. The method of claim 5 wherein said amine is triphenylamine.

7. The method of claim 1 wherein said columns further comprise $C_8$ reversed phase resins.

8. The method of claim 1 wherein said target analytes are collected from said column separation step as an eluate and further comprising treating the eluate from said column separation to reduce the volume of the eluate by evaporating a portion of the volatile components thereof and thereafter reconstituting a part of said evaporated volume with a phosphate buffer.

9. The method of claim 1 wherein the step of providing a sample of newborn meconium comprises collecting and pooling meconium produced by an infant newborn from birth until just prior to the appearance of a transitional milk stool; and vigorously mixing the pooled and collected meconium until a substantially uniform, non-striated, smooth semi-solid meconium product having a putty-like consistency is obtained and selecting said test sample from a portion of said mixed semi-solid meconium product.

10. The method of claim 9 wherein the step of agitating the first mixture includes homogenizing the first mixture by subjecting the first mixture to high shear blade processing to finely subdivide the meconium component.

11. The method of claim 10 wherein said homogenizing step is performed in a tissue homogenizer and the pooled meconium is homogenized for a time sufficient to provide a substantially uniform homogenate.

12. The method of claim 11 wherein said uniform meconium homogenate is characterized by having an average particle size of less than about 10.0 microns.

13. The method of claim 12 wherein said meconium is homogenized until a substantially uniform homogenate having an average particle size of from about 2.0 to about 5.0 microns is obtained.

14. The method of claim 1 wherein the column separated target analytes are analyzed by a method selected from the group consisting of enzyme multiplied immunoassay, fluorescence polarization immunoassay and gas chromatography/mass spectrometry analysis methods.

15. The method of claim 1 wherein the column separated target analytes include, to the extent said analytes are present in the meconium sample, target analytes from the group consisting of cocaine metabolites, opiates, cannibinoids, amphetamines, phencyclidine, methadone, barbituates, benzodiazepines, methaqualone, and propoxyphene and mixtures thereof.

16. A method for preparing a concentrated meconium extract containing basic and acidic-neutral target analytes present, if any, in a sample of meconium suspected of containing said target analyte(s), said method comprising:

providing a test sample of meconium suspected of containing a said target analyte;

adding a substantially non-aqueous methanol solution to the test sample to form a first mixture;

agitating the first mixture for a time sufficient to release substantially all of said target analyte from the meconium sample, until a substantially homogeneous mixture is obtained including a liquid organic phase component and a second phase;

separating the liquid organic component phase from the mixture;

adding an acidic phosphate buffer to the separated liquid organic component phase to provide a buffered specimen;

reducing an amount of residual lipid, if any, present in said buffered specimen by passing the buffered specimen through at least one mixed mode extraction column; and sequentially eluting extracted acidic-neutral and basic target analytes from said extraction column to provide a purified cocktail extract eluate comprising a solution of basic and acidic-neutral target analytes suitable for use in qualitative and quantitative analyses for the presence of said target analytes, wherein a negative bias caused by the presence of interfering residual lipids is reduced or eliminated.

* * * * *